United States Patent
Khabar et al.

(10) Patent No.: US 9,677,071 B2
(45) Date of Patent: Jun. 13, 2017

(54) MULTIPLE INTERFERON AND VIRUS RESPONSE ELEMENT CELL-BASED FLUORESCENCE SYSTEM

(75) Inventors: Khalid S. A. Khabar, Riyadh (SA); Fahad Nasser Al-Majhdi, Riyadh (SA)

(73) Assignees: KING FAISAL SPECIALIST HOSPITAL AND RESEARCH CENTRE, Riyadh (SA); KING SAUD UNIVERSITY, Riyadh (SA)

(*) Notice: Subject to any disclaimer, the term of this patent is extended or adjusted under 35 U.S.C. 154(b) by 449 days.

(21) Appl. No.: 14/112,773

(22) PCT Filed: Apr. 20, 2011

(86) PCT No.: PCT/EP2011/002029
§ 371 (c)(1),
(2), (4) Date: Jan. 4, 2014

(87) PCT Pub. No.: WO2012/143020
PCT Pub. Date: Oct. 26, 2012

(65) Prior Publication Data
US 2014/0128286 A1    May 8, 2014

(51) Int. Cl.
| | | |
|---|---|---|
| C12N 15/00 | (2006.01) | |
| C12N 5/00 | (2006.01) | |
| C12N 5/02 | (2006.01) | |
| C40B 40/08 | (2006.01) | |
| C40B 30/06 | (2006.01) | |
| C12N 15/10 | (2006.01) | |
| C12Q 1/68 | (2006.01) | |

(52) U.S. Cl.
CPC ....... *C12N 15/1086* (2013.01); *C12Q 1/6897* (2013.01); *C12Q 1/6837* (2013.01); *G01N 2333/005* (2013.01); *G01N 2333/555* (2013.01)

(58) Field of Classification Search
None
See application file for complete search history.

(56) References Cited

U.S. PATENT DOCUMENTS

2010/0203067 A1* 8/2010 Spencer ............... C12N 5/0639
424/184.1

OTHER PUBLICATIONS

Al-Haj, L. et al., "Cloning-free regulated monitoring of reporter and gene expression," *BMC Molecular Biology*, 2009, vol. 10, No. 20, p. 1-13.
Fujii, Y. et al., "Crystal structure of an IRF-DNA complex reveals novel DNA recognition and cooperative binding to a tandem repeat of core sequences," *The EMBO Journal*, 1999, vol. 18, No. 18, p. 5028-5041.
Génin, P. et al., "The role of differential expression of human interferon-A genes in antiviral immunity," *Cytokine & Growth Factor Reviews*, 2009, vol. 20, p. 283-295.
Khabar, K. et al., "Expressed Gene Clusters Associated with Cellular Sensitivity and Resistance Towards Anti-viral and Anti-proliferative Actions of Interferon," *Journal of Molecular Biology*, 2004, vol. 342, p. 833-846.
Mahmoud, L. et al., "Green Fluorescent Protein Reporter System with Transcriptional Sequence Heterogeneity for Monitoring the Interferon Response," *Journal of Virology*, 2011, vol. 85, No. 18, p. 9268-9275.
Savitsky, D. et al., "Regulation of immunity and oncogenesis by the IRF transcription factor family," *Cancer, Immunology, Immunotherapy*, 2010, vol. 59, p. 489-510.

* cited by examiner

*Primary Examiner* — Channing S Mahatan
(74) *Attorney, Agent, or Firm* — Saliwanchik, Lloyd & Eisenschenk

(57) ABSTRACT

The present disclosure refers to a method for a specific, versatile and sensitive detection of IFN-/virus-induced genes, a method for quantifying IFN potency and activity in a pharmaceutical preparation or biological sample, a method for distinguishing between IFN- and viral induction, and/or for distinguishing between different viruses, and a method for the quantification of virus activity. Also, the invention provides the necessary molecular tools like expression active response constructs, suitable cell lines, an array to perform the method and a kit.

23 Claims, 10 Drawing Sheets

FIGURE 6

| IFN NDV | | IFN NDV | |
|---|---|---|---|
| | IFIT2-V | | VREL-1 |
| | AB-VRE | | IFIT2 |
| | VRE CON | | GAS-2 |
| | IFNA4 | | TMEM67-V |
| | NFKBI | | TMEM67 |
| | IFNB-2 | | GAS |
| | GPB1-V | | IRF-7-V |
| | IFIT-M | | MATR3-3 |
| | IFNB | | NT5C3-2 |
| | IFNO-V | | GPB3-AV |
| | CXCL10A | | CASP7-2 |
| | PSMP9-V | | CASP7-3 |
| | USB18-V | | CASP7-4 |
| | SELPLG-M | | NT5C3-3 |
| | PKR-1 | | DZIP1(2) |
| | C100 RF18 | | SAMD9 |
| | C130RF18-V | | GIP3-6-1 |
| | IFIT2-V L | | VREL-2 |
| | CI30RF18 C | | PARP10 |
| | OASI | | STAT1 |
| | IFIT3-1 | | PLSCR1V |
| | HERC5 | | IFI27-2V |
| | MATR3-1 | | DZIP1 |
| | CXCL10B | | IFIH1 |
| | IF144-2 | | MATR3-2 |
| | ISG15 | | MX1-2 |
| | OAS1-V L | | IFNA-V |
| | DDX58 | | IFNA5 |
| | IFIT3-2 | | RGS20-V |
| | NT5C3-1 | | CASP7-1 |
| | ISRE-74 | | PKR-V |
| | PRD2X | | IFIT1 |
| | ISG15-V | | ISRE-74 |
| | USP18 | | MX1 |
| | USB18-M | | EPSTI1 |
| | ISG15-M | | 7VRE2 |
| | IF144 | | PSMP8 |
| | OAS3V | | SP100 |
| | IFITM 1-V | | IFI27-1 |
| | | | VREL-3 |
| | | | TAP1 |
| | | | 7XVRE1 |
| | | | GPB3-BV |

30　　　　　　　　　　1　↑ Fold

SEQUENCE LISTING

```
<160> NUMBER OF SEQ ID NOS: 111

<210> SEQ ID NO 1
<211> LENGTH: 12
<212> TYPE: DNA
<213> ORGANISM: Homo sapiens
<220> FEATURE:
<221> NAME/KEY: misc_feature
<222> LOCATION: (5)..(6)
<223> OTHER INFORMATION: n is a, c, g, t or u

<400> SEQUENCE: 1
gaaanngaaa sy                                                            12

<210> SEQ ID NO 2
<211> LENGTH: 13
<212> TYPE: DNA
<213> ORGANISM: Homo sapiens
<220> FEATURE:
<221> NAME/KEY: misc_feature
<222> LOCATION: (6)..(7)
<223> OTHER INFORMATION: n is a, c, g, t or u

<400> SEQUENCE: 2
gaaaanngaa asy                                                           13

<210> SEQ ID NO 3
<211> LENGTH: 14
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: misc_feature
<222> LOCATION: (7)..(8)
<223> OTHER INFORMATION: n is a, c, g, t or u

<400> SEQUENCE: 3
rngaaannga aact                                                          14

<210> SEQ ID NO 4
<211> LENGTH: 57
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 4
gggaaaccga aactggggaa accgaaactg gggaaaccga aactgggaaa ccgaaac           57

<210> SEQ ID NO 5
<211> LENGTH: 62
<212> TYPE: DNA
<213> ORGANISM: Artificial sequence
<220> FEATURE:
<223> OTHER INFORMATION: synthetic VRE (virus responsive element)
``` derived from natural sequence

<400> SEQUENCE: 5
ggaaaccgaa aggggaaagt gaaactaaag ctgaaaccga aaggggaaag tgaaactaaa    60
gc    62

<210> SEQ ID NO 6
<211> LENGTH: 56
<212> TYPE: DNA
<213> ORGANISM: Homo sapiens

<400> SEQUENCE: 6
gggaaaatga aactcggagc tgggagagag gggaaaatga aactgcagaa atagaa    56

<210> SEQ ID NO 7
<211> LENGTH: 49
<212> TYPE: DNA
<213> ORGANISM: Homo sapiens

<400> SEQUENCE: 7
gctaggtttc gtttctgcgc cccacagggt ctgtgagttt catttcttc    49

<210> SEQ ID NO 8
<211> LENGTH: 54
<212> TYPE: DNA
<213> ORGANISM: Homo sapiens

<400> SEQUENCE: 8
tgagtttcgt ttctgagctc ctttcatttt caccggtttc aattctcctc tgga    54

<210> SEQ ID NO 9
<211> LENGTH: 54
<212> TYPE: DNA
<213> ORGANISM: Artificial sequence
<220> FEATURE:
<223> OTHER INFORMATION: modified sequence from natural ISRE/VRE

<400> SEQUENCE: 9
ctcccggcgc ggaggccgct gtaagtttcg ctttccattc agtggaaaac gaaa    54

<210> SEQ ID NO 10
<211> LENGTH: 76
<212> TYPE: DNA
<213> ORGANISM: Homo sapiens

<400> SEQUENCE: 10
gattctgttt cagtttcccc tcaagaggga tcttgatagg gttccatcag tttcactttc    60
ctttcccctt tcatcc    76

<210> SEQ ID NO 11
<211> LENGTH: 50
<212> TYPE: DNA
<213> ORGANISM: Homo sapiens

<400> SEQUENCE: 11
cctccttccg tctttcagtt tcacttttgt tttcctgctc ctgctccctc    50

<210> SEQ ID NO 12
<211> LENGTH: 61
<212> TYPE: DNA
<213> ORGANISM: Homo sapiens

<400> SEQUENCE: 12

```
gtttcatttt cctcctccca acgattttaa attagtttca ctttccagtt tcctcttcct    60
t                                                                    61

<210> SEQ ID NO 13
<211> LENGTH: 50
<212> TYPE: DNA
<213> ORGANISM: Homo sapiens

<400> SEQUENCE: 13
aaaaaactga aactcagcct gaaagatgaa cagaacaaaa cagaaatcct              50

<210> SEQ ID NO 14
<211> LENGTH: 40
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 14
gaaagtgaaa agagaaatgg aaagtggaaa aggagaaact                         40

<210> SEQ ID NO 15
<211> LENGTH: 51
<212> TYPE: DNA
<213> ORGANISM: Homo sapiens

<400> SEQUENCE: 15
agtgtctgat ttgcaaaagg aaagtgcaaa gacagctcct cccttctgag g             51

<210> SEQ ID NO 16
<211> LENGTH: 51
<212> TYPE: DNA
<213> ORGANISM: Homo sapiens

<400> SEQUENCE: 16
ttcggagagc cgggcgggaa aacgaaacca gaaatccgaa ggccgcgcca g             51

<210> SEQ ID NO 17
<211> LENGTH: 52
<212> TYPE: DNA
<213> ORGANISM: Homo sapiens

<400> SEQUENCE: 17
gctaggtttc gtttctgcgc cccacagggt ctgtgagttt catttcttcg cg            52

<210> SEQ ID NO 18
<211> LENGTH: 55
<212> TYPE: DNA
<213> ORGANISM: Homo sapiens

<400> SEQUENCE: 18
tgagtttcgt ttctgagctc ctttcatttt caccggtttc aattctcctc tggag         55

<210> SEQ ID NO 19
<211> LENGTH: 56
<212> TYPE: DNA
<213> ORGANISM: Artificial sequence
<220> FEATURE:
<223> OTHER INFORMATION: modified sequence from natural ISRE/VRE

<400> SEQUENCE: 19
ctccttccgt ctttcagttt cactttgtt ttcctgctca gtttcacttt tgtttt         56
```

```
<210> SEQ ID NO 20
<211> LENGTH: 48
<212> TYPE: DNA
<213> ORGANISM: Homo sapiens

<400> SEQUENCE: 20
cagcttcagt tttcctaatg acagtgagtc atttcttctc tctctttt            48

<210> SEQ ID NO 21
<211> LENGTH: 53
<212> TYPE: DNA
<213> ORGANISM: Homo sapiens

<400> SEQUENCE: 21
ccatttccct ccctcctctc atagacaacc gatatatatc tttcactttg gtg       53

<210> SEQ ID NO 22
<211> LENGTH: 61
<212> TYPE: DNA
<213> ORGANISM: Homo sapiens

<400> SEQUENCE: 22
gtttcatttt cctcctccca acgattttaa attagtttca ctttccagtt tcctcttcct   60
t                                                                  61

<210> SEQ ID NO 23
<211> LENGTH: 72
<212> TYPE: DNA
<213> ORGANISM: Artificial sequence
<220> FEATURE:
<223> OTHER INFORMATION: modified sequence from natural ISRE/VRE

<400> SEQUENCE: 23
gattctgttt cagttttcccc tcagtttcac tttccttttcc cctttcagca gtttcacttt   60
cctttcccct tt                                                      72

<210> SEQ ID NO 24
<211> LENGTH: 54
<212> TYPE: DNA
<213> ORGANISM: Homo sapiens

<400> SEQUENCE: 24
tccgctagct ttagtttcac tttcccctttt cggtttccct aggtttccaa cttg        54

<210> SEQ ID NO 25
<211> LENGTH: 53
<212> TYPE: DNA
<213> ORGANISM: Homo sapiens

<400> SEQUENCE: 25
agtcctgcca atttcacttt ctagtttcac tttccctttt gtaacgtcag ctg          53

<210> SEQ ID NO 26
<211> LENGTH: 69
<212> TYPE: DNA
<213> ORGANISM: Homo sapiens

<400> SEQUENCE: 26
ccttctcttt cccttttccag cactttgatt ccttgtggtg tctgtttctg ttttgttagt   60
aatttcatg                                                          69
```

<210> SEQ ID NO 27
<211> LENGTH: 53
<212> TYPE: DNA
<213> ORGANISM: Homo sapiens

<400> SEQUENCE: 27
atctccatca aaccaagatc ctaagggctg gaagtttgtc ttttccatca ttg        53

<210> SEQ ID NO 28
<211> LENGTH: 51
<212> TYPE: DNA
<213> ORGANISM: Homo sapiens

<400> SEQUENCE: 28
aaagtttgac tttctctgca cagttccact ttcagagttt tgcttttgtt g          51

<210> SEQ ID NO 29
<211> LENGTH: 65
<212> TYPE: DNA
<213> ORGANISM: Homo sapiens

<400> SEQUENCE: 29
tctcattttc atttttacct gttttgtctt actttgtact ttacccagtt tcgctttatc    60
atctg                                                                65

<210> SEQ ID NO 30
<211> LENGTH: 50
<212> TYPE: DNA
<213> ORGANISM: Homo sapiens

<400> SEQUENCE: 30
gatgatcttt ccacttcctg gtttttctga ctttttttct ttttgcagtg              50

<210> SEQ ID NO 31
<211> LENGTH: 54
<212> TYPE: DNA
<213> ORGANISM: Homo sapiens

<400> SEQUENCE: 31
gtttcctttt cctttttcgat tccgccccct aacattatgt ttcgttttcc actg        54

<210> SEQ ID NO 32
<211> LENGTH: 51
<212> TYPE: DNA
<213> ORGANISM: Homo sapiens

<400> SEQUENCE: 32
ccagctcccg gcgcggaggc cgctgtaagt ttcgctttcc attcagtgga g            51

<210> SEQ ID NO 33
<211> LENGTH: 52
<212> TYPE: DNA
<213> ORGANISM: Homo sapiens

<400> SEQUENCE: 33
gctaggtttc gtttctgcgc cccacagggt ctgtgagttt catttcttcg cg           52

<210> SEQ ID NO 34
<211> LENGTH: 55
<212> TYPE: DNA
<213> ORGANISM: Homo sapiens

<400> SEQUENCE: 34
tgagtttcgt ttctgagctc ctttcatttt caccggtttc aattctcctc tggag        55

<210> SEQ ID NO 35
<211> LENGTH: 52
<212> TYPE: DNA
<213> ORGANISM: Homo sapiens

<400> SEQUENCE: 35
gggctgggca cactgagttt cagtttcctt tctctgagtc tttgaagctt cg           52

<210> SEQ ID NO 36
<211> LENGTH: 51
<212> TYPE: DNA
<213> ORGANISM: Homo sapiens

<400> SEQUENCE: 36
ggtaaatgtc tttctgcttt tcattttcc tagctagcat tagtctctct g             51

<210> SEQ ID NO 37
<211> LENGTH: 51
<212> TYPE: DNA
<213> ORGANISM: Homo sapiens

<400> SEQUENCE: 37
ccgctagttg cactttcgat tttcccttta gttattaaag ttcctatgca g            51

<210> SEQ ID NO 38
<211> LENGTH: 57
<212> TYPE: DNA
<213> ORGANISM: Homo sapiens

<400> SEQUENCE: 38
agtccccgcc acttttgctt ttccctgtct ttcggtcatt cggttttgtt tcttccg      57

<210> SEQ ID NO 39
<211> LENGTH: 53
<212> TYPE: DNA
<213> ORGANISM: Homo sapiens

<400> SEQUENCE: 39
gctgcctttt ctcctgccgg gtagtttcgc tttcctgcgc agagtctgcg gag          53

<210> SEQ ID NO 40
<211> LENGTH: 51
<212> TYPE: DNA
<213> ORGANISM: Homo sapiens

<400> SEQUENCE: 40
cctccttccg tctttcagtt tcacttttgt tttcctgctc ctgctccctc g            51

<210> SEQ ID NO 41
<211> LENGTH: 58
<212> TYPE: DNA
<213> ORGANISM: Homo sapiens

<400> SEQUENCE: 41
aattcgcttt cctttctgt ttcccgcggt gtccttaacc aaaggcctcc tctcttca     58

<210> SEQ ID NO 42
<211> LENGTH: 54
<212> TYPE: DNA
<213> ORGANISM: Homo sapiens -continued

<400> SEQUENCE: 42
tgatatctta ttgtggtttt gctttgcatt tccctgtgag cacctttca tatg    54

<210> SEQ ID NO 43
<211> LENGTH: 58
<212> TYPE: DNA
<213> ORGANISM: Homo sapiens

<400> SEQUENCE: 43
cacttctttc aaagtggttt ctttcagttt tcctattaag ttcctgtgtt gcttcttg    58

<210> SEQ ID NO 44
<211> LENGTH: 54
<212> TYPE: DNA
<213> ORGANISM: Homo sapiens

<400> SEQUENCE: 44
agttttctgt cataatttct tttctaccct tttctctttg ctccttctga gaca    54

<210> SEQ ID NO 45
<211> LENGTH: 58
<212> TYPE: DNA
<213> ORGANISM: Homo sapiens

<400> SEQUENCE: 45
ccattctttt attcctttac ctttgctttc actttactct acccttaatt ctttcttg    58

<210> SEQ ID NO 46
<211> LENGTH: 59
<212> TYPE: DNA
<213> ORGANISM: Homo sapiens

<400> SEQUENCE: 46
actctttgct atttagtttc attttgttt taagtttcac tttgcagctg tttctttt    59

<210> SEQ ID NO 47
<211> LENGTH: 52
<212> TYPE: DNA
<213> ORGANISM: Homo sapiens

<400> SEQUENCE: 47
aggttcctct tttctttcca gagccagttg acagatttac cttctcttta ag    52

<210> SEQ ID NO 48
<211> LENGTH: 61
<212> TYPE: DNA
<213> ORGANISM: Homo sapiens

<400> SEQUENCE: 48
acagttttag ctttacaatt tttttctct ttccttttgt tgtgaattca tttacctaac    60
g    61

<210> SEQ ID NO 49
<211> LENGTH: 60
<212> TYPE: DNA
<213> ORGANISM: Homo sapiens

<400> SEQUENCE: 49
atttgacttc ctctttcct aactgaatac tctttatttc tttatcctgc ctaagaactt    60

<210> SEQ ID NO 50
<211> LENGTH: 61

```
<212> TYPE: DNA
<213> ORGANISM: Homo sapiens

<400> SEQUENCE: 50
caatttcact tttattcctc tttcttctcc ttacctattt ttgacacatt tattcagtat      60
g                                                                      61

<210> SEQ ID NO 51
<211> LENGTH: 54
<212> TYPE: DNA
<213> ORGANISM: Homo sapiens

<400> SEQUENCE: 51
ctgtggcttt cgctttcact tcctcctctt tcgctttcac ttcctccccg agag            54

<210> SEQ ID NO 52
<211> LENGTH: 64
<212> TYPE: DNA
<213> ORGANISM: Artificial sequence
<220> FEATURE:
<223> OTHER INFORMATION: synthetic ISRE (IFN-responsive element)
      derived from natural sequence

<400> SEQUENCE: 52
agctttagtt tcactttccc ctttcggttt cagctttagt ttcactttcc cctttcggtt      60
tccg                                                                   64

<210> SEQ ID NO 53
<211> LENGTH: 60
<212> TYPE: DNA
<213> ORGANISM: Homo sapiens

<400> SEQUENCE: 53
gggaaaatga aactcggagc tgggagagag gggaaaatga aactgcagaa atagaaactg      60

<210> SEQ ID NO 54
<211> LENGTH: 54
<212> TYPE: DNA
<213> ORGANISM: Homo sapiens

<400> SEQUENCE: 54
aagtaaagaa agtgaaagtg aaaaggagat tggaaagcaa ggaaaggaga aacg            54

<210> SEQ ID NO 55
<211> LENGTH: 43
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 55
gaaagtgaaa gtgaaagtga aagtgaaagt gaaagtgaaa gtg                        43

<210> SEQ ID NO 56
<211> LENGTH: 51
<212> TYPE: DNA
<213> ORGANISM: Artificial sequence
<220> FEATURE:
<223> OTHER INFORMATION: modified sequence from natural ISRE/VRE

<400> SEQUENCE: 56
gaaagtgaaa agagaattgg aaagcgaaag tgaaaagaga attggaaagc g               51
```

<210> SEQ ID NO 57
<211> LENGTH: 47
<212> TYPE: DNA
<213> ORGANISM: Artificial sequence
<220> FEATURE:
<223> OTHER INFORMATION: synthetic VRE (virus responsive element)
derived from natural sequence

<400> SEQUENCE: 57
aagtgaaagt gaaagtgaaa gtgaaagtga aagtgaaagt gaaagtg                47

<210> SEQ ID NO 58
<211> LENGTH: 53
<212> TYPE: DNA
<213> ORGANISM: Artificial sequence
<220> FEATURE:
<223> OTHER INFORMATION: synthetic VRE (virus responsive element)
derived from natural sequence

<400> SEQUENCE: 58
agaaatggaa agtagaaatg gaaagtgaga agtgaaagtg agaagtgaaa gtg          53

<210> SEQ ID NO 59
<211> LENGTH: 56
<212> TYPE: DNA
<213> ORGANISM: Artificial sequence
<220> FEATURE:
<223> OTHER INFORMATION: synthetic VRE (virus responsive element)
derived from natural sequence

<400> SEQUENCE: 59
gggaaagaga aaccggaaaa gcgaaactgg aaagagaaac cggaaaagcg aaactg       56

<210> SEQ ID NO 60
<211> LENGTH: 70
<212> TYPE: DNA
<213> ORGANISM: Artificial sequence
<220> FEATURE:
<223> OTHER INFORMATION: modified sequence from natural ISRE/VRE

<400> SEQUENCE: 60
acttttgctt ttccctgtct ttcggtcatt cggttttgtt tcttccggga aagggaaacc   60
gaaactgaag                                                         70

<210> SEQ ID NO 61
<211> LENGTH: 75
<212> TYPE: DNA
<213> ORGANISM: Artificial sequence
<220> FEATURE:
<223> OTHER INFORMATION: modified sequence from natural ISRE/VRE

<400> SEQUENCE: 61
aagaaaaaga gtcctgccaa tttcactttc tagtttcact ttcccttttg ttgaagggaa   60
acaaacaaaa aggaa                                                   75

<210> SEQ ID NO 62
<211> LENGTH: 74
<212> TYPE: DNA
<213> ORGANISM: Homo sapiens

<400> SEQUENCE: 62
gagaaacata aagagtgcat gaaggaaagc aaaaacagaa atggaaagtg gcccattaag   60
aaagtggaaa tcag                                                    74

<210> SEQ ID NO 63
<211> LENGTH: 66
<212> TYPE: DNA
<213> ORGANISM: Homo sapiens

<400> SEQUENCE: 63
cacaaatgaa aacagtaaaa gaaactgaaa gtacagagaa atgttcagaa aatgaaaacc    60
atgtgt    66

<210> SEQ ID NO 64
<211> LENGTH: 69
<212> TYPE: DNA
<213> ORGANISM: Homo sapiens

<400> SEQUENCE: 64
tagaaagagc ataaaagaaa gcaaaaagag aagtagaaag taggcaagaa aatggaaact    60
gtgaccttg    69

<210> SEQ ID NO 65
<211> LENGTH: 60
<212> TYPE: DNA
<213> ORGANISM: Homo sapiens

<400> SEQUENCE: 65
cagcaaagtg gaacttaaga ggggaagtga acagggaaa tgcaaggaga aaggcgaaag    60

<210> SEQ ID NO 66
<211> LENGTH: 63
<212> TYPE: DNA
<213> ORGANISM: Homo sapiens

<400> SEQUENCE: 66
ctgaaagatg actcagttaa gaagctggaa aataaaacca ggtcttattc tgaactgaaa    60
gtc    63

<210> SEQ ID NO 67
<211> LENGTH: 62
<212> TYPE: DNA
<213> ORGANISM: Artificial sequence
<220> FEATURE:
<223> OTHER INFORMATION: modified sequence from natural ISRE/VRE

<400> SEQUENCE: 67
agatgggcac tgtttcttat cccaatttta cagatgggaa aactgaagct cagggaggca    60
ag    62

<210> SEQ ID NO 68
<211> LENGTH: 61
<212> TYPE: DNA
<213> ORGANISM: Homo sapiens

<400> SEQUENCE: 68
agtagaaaag agcaagtcta aggaatatct agaaagagg aagttagaac catagaaaag    60
g    61

<210> SEQ ID NO 69
<211> LENGTH: 61
<212> TYPE: DNA
<213> ORGANISM: Homo sapiens

<400> SEQUENCE: 69

```
tgaattattt ctcctccttc aatttcagtt tgctcatact ttgtgacttg cggtcacagt    60
g                                                                    61

<210> SEQ ID NO 70
<211> LENGTH: 52
<212> TYPE: DNA
<213> ORGANISM: Homo sapiens

<400> SEQUENCE: 70 atgagggag aaagatgtct gcagtttcgg tttcctggaa aatgaaacct gg             52

<210> SEQ ID NO 71
<211> LENGTH: 51
<212> TYPE: DNA
<213> ORGANISM: Homo sapiens

<400> SEQUENCE: 71
agtgtctgat ttgcaaaagg aaagtgcaaa gacagctcct cccttctgag g             51

<210> SEQ ID NO 72
<211> LENGTH: 51
<212> TYPE: DNA
<213> ORGANISM: Homo sapiens

<400> SEQUENCE: 72
tgtaaatgga aaacgaaat gacaaataat tatgaaagag gcatccattt g              51

<210> SEQ ID NO 73
<211> LENGTH: 50
<212> TYPE: DNA
<213> ORGANISM: Homo sapiens

<400> SEQUENCE: 73
tgagcaggcg gccgctttcg atttcgcttt cccctaaatg gctgagcttg               50

<210> SEQ ID NO 74
<211> LENGTH: 41
<212> TYPE: DNA
<213> ORGANISM: Homo sapiens

<400> SEQUENCE: 74
cagccattta ggggaaagcg aaatcgaaag cggccgcctg g                        41

<210> SEQ ID NO 75
<211> LENGTH: 56
<212> TYPE: DNA
<213> ORGANISM: Homo sapiens

<400> SEQUENCE: 75
acagcaggaa atagaaactt aagagaaata cacacttctg agaaactgaa acgacg        56

<210> SEQ ID NO 76
<211> LENGTH: 44
<212> TYPE: DNA
<213> ORGANISM: Homo sapiens

<400> SEQUENCE: 76
tgcctcggga aagggaaacc gaaactgaag ccaaatttgg ccag                     44

<210> SEQ ID NO 77
<211> LENGTH: 48
<212> TYPE: DNA
```

<213> ORGANISM: Homo sapiens

<400> SEQUENCE: 77
tgtaacgtca gctgaaggga acaaacaaa aaggaaccag aggccacg        48

<210> SEQ ID NO 78
<211> LENGTH: 51
<212> TYPE: DNA
<213> ORGANISM: Homo sapiens

<400> SEQUENCE: 78
aaaaaactga aactcagcct gaaagatgaa cagaacaaaa cagaaatcct g        51

<210> SEQ ID NO 79
<211> LENGTH: 51
<212> TYPE: DNA
<213> ORGANISM: Homo sapiens

<400> SEQUENCE: 79
acacggttat agacaaagaa aaaactgaaa cccagcatca aagaggaaca g        51

<210> SEQ ID NO 80
<211> LENGTH: 51
<212> TYPE: DNA
<213> ORGANISM: Homo sapiens

<400> SEQUENCE: 80
tacaaaatgg aaaaacagaa caaaacagaa aacctaaagc tgtattgctg g        51

<210> SEQ ID NO 81
<211> LENGTH: 56
<212> TYPE: DNA
<213> ORGANISM: Homo sapiens

<400> SEQUENCE: 81
agtagtaagt tttgctttac aaattcttac attgcagaat cgtctgcatc agctag        56

<210> SEQ ID NO 82
<211> LENGTH: 51
<212> TYPE: DNA
<213> ORGANISM: Homo sapiens

<400> SEQUENCE: 82
cgccagcgcg ggaaccggga aaaggaaacc gtgttgtgta cgtaagattc g        51

<210> SEQ ID NO 83
<211> LENGTH: 36
<212> TYPE: DNA
<213> ORGANISM: Homo sapiens

<400> SEQUENCE: 83
gctgctagaa agaaacgaaa ctgaaagcag ggaatg        36

<210> SEQ ID NO 84
<211> LENGTH: 47
<212> TYPE: DNA
<213> ORGANISM: Homo sapiens

<400> SEQUENCE: 84
ctttgtaggt ttttgttttc ttttgatttc agtttccatt tcctctg        47

<210> SEQ ID NO 85
<211> LENGTH: 58

<212> TYPE: DNA
<213> ORGANISM: Homo sapiens

<400> SEQUENCE: 85
gttaaatact ttcacttctc ttttccccat ttgggcggag ccctttctga gtcagtcg    58

<210> SEQ ID NO 86
<211> LENGTH: 63
<212> TYPE: DNA
<213> ORGANISM: Homo sapiens

<400> SEQUENCE: 86
tgcagggaag taccgggaag gactttccag cgcagggagt ttctccgctt ggaaattccc    60
cgg    63

<210> SEQ ID NO 87
<211> LENGTH: 42
<212> TYPE: DNA
<213> ORGANISM: Homo sapiens

<400> SEQUENCE: 87
gtaacaaaag cgaaactcca tctcaaaaaa agaaacgcaa gg    42

<210> SEQ ID NO 88
<211> LENGTH: 61
<212> TYPE: DNA
<213> ORGANISM: Homo sapiens

<400> SEQUENCE: 88
aaatgtaaat gacataggaa aactgaaagg gagaagtgaa agtgggaaat tcctctgaat    60
g    61

<210> SEQ ID NO 89
<211> LENGTH: 59
<212> TYPE: DNA
<213> ORGANISM: Homo sapiens

<400> SEQUENCE: 89
ctaaaatgta aatgacatag gaaaactgaa agggagaagt gaaagtggga aattcctct    59

<210> SEQ ID NO 90
<211> LENGTH: 40
<212> TYPE: DNA
<213> ORGANISM: Homo sapiens

<400> SEQUENCE: 90
tgctattatg aaggaaaaaa gtgaaatgga aattaaaaac    40

<210> SEQ ID NO 91
<211> LENGTH: 29
<212> TYPE: DNA
<213> ORGANISM: Homo sapiens

<400> SEQUENCE: 91
ctcgggaaag ggaaaccgaa actgaagcc    29

<210> SEQ ID NO 92
<211> LENGTH: 48
<212> TYPE: DNA
<213> ORGANISM: Homo sapiens

<400> SEQUENCE: 92

```
agcctgattt ccccgaaatg acggcagcct gatttccccg aaatgacg                         48

<210> SEQ ID NO 93
<211> LENGTH: 69
<212> TYPE: DNA
<213> ORGANISM: Homo sapiens

<400> SEQUENCE: 93
tttcagaaac agttcatgtt ttggaaagtg aaacctaatt cactattacc aaaaaaagag          60
gagcagagg                                                                   69

<210> SEQ ID NO 94
<211> LENGTH: 65
<212> TYPE: DNA
<213> ORGANISM: Homo sapiens

<400> SEQUENCE: 94
tgatgttttc attcagggac ttgaaacttg ttttaacaca tgagcaatgt tttccctcaa          60
aatag                                                                       65

<210> SEQ ID NO 95
<211> LENGTH: 50
<212> TYPE: DNA
<213> ORGANISM: Homo sapiens

<400> SEQUENCE: 95
aaggccctcc ctggaggaga actgaaactt agggtgggga ctgtagaaag                      50

<210> SEQ ID NO 96
<211> LENGTH: 48
<212> TYPE: DNA
<213> ORGANISM: Homo sapiens

<400> SEQUENCE: 96
agggcggcgc agggcggcgc ttctcggaaa gcgaaagccg gcggggcg                        48

<210> SEQ ID NO 97
<211> LENGTH: 40
<212> TYPE: DNA
<213> ORGANISM: Homo sapiens

<400> SEQUENCE: 97
cttctgagtc ttagagaaaa aggaactgga gccccagacc                                 40

<210> SEQ ID NO 98
<211> LENGTH: 50
<212> TYPE: DNA
<213> ORGANISM: Homo sapiens

<400> SEQUENCE: 98
aacacatgta gagagtgcaa aagaaagca aaaacagaca tagaaagtaa                       50

<210> SEQ ID NO 99
<211> LENGTH: 46
<212> TYPE: DNA
<213> ORGANISM: Homo sapiens

<400> SEQUENCE: 99
gagtgcatga aggaaagcaa aaacagaaat ggaaagtggc ccagaa                          46

<210> SEQ ID NO 100
<211> LENGTH: 57
```

```
<212> TYPE: DNA
<213> ORGANISM: Artificial sequence
<220> FEATURE:
<223> OTHER INFORMATION: synthetic VRE (virus-responsive element)
      derived from natural sequence

<400> SEQUENCE: 100
gggaaaccga aagtgggaaa ccgaaagtgg gaaaccgaaa gtgggaaacc gaaagtg        57

<210> SEQ ID NO 101
<211> LENGTH: 54
<212> TYPE: DNA
<213> ORGANISM: Artificial sequence
<220> FEATURE:
<223> OTHER INFORMATION: synthetic ISRE (IFN-responsive element)

<400> SEQUENCE: 101
tactttcgct ttccactttc gctttcctca ctttcgcttt cctactttcg cttt           54

<210> SEQ ID NO 102
<211> LENGTH: 57
<212> TYPE: DNA
<213> ORGANISM: Artificial sequence
<220> FEATURE:
<223> OTHER INFORMATION: synthetic ISRE (IFN-responsive element) derived
      from natural sequence

<400> SEQUENCE: 102
gggaaaccga aactaggaaa ccgaaactga ggaaaccgaa actggaaacc gaaacta        57

<210> SEQ ID NO 103
<211> LENGTH: 40
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 103
gagaagtgaa agtgagaagt gaaagtgaga agtgaaagtg                           40

<210> SEQ ID NO 104
<211> LENGTH: 53
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 104
agaaatggaa agtgagaagt gaaagtagaa atggaaagtg agaagtgaaa gtg            53

<210> SEQ ID NO 105
<211> LENGTH: 57
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 105
agaaatggaa agtagaaatg gaaagtactg cgagaagtga agtgagaag tgaaagt         57

<210> SEQ ID NO 106
<211> LENGTH: 51
<212> TYPE: DNA
<213> ORGANISM: Homo sapiens
```

<400> SEQUENCE: 106
agtgtctgat ttgcaaaagg aaagtgcaaa gacagctcct cccttctgag g    51

<210> SEQ ID NO 107
<211> LENGTH: 36
<212> TYPE: DNA
<213> ORGANISM: Homo sapiens

<400> SEQUENCE: 107
gctgctagaa agaaacgaaa ctgaaagcag ggaatg    36

<210> SEQ ID NO 108
<211> LENGTH: 57
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 108
gggaaaccga aagtaggaaa ccgaaagtga ggaaaccgaa agtggaaacc gaaagta    57

<210> SEQ ID NO 109
<211> LENGTH: 57
<212> TYPE: DNA
<213> ORGANISM: Artificial sequence
<220> FEATURE:
<223> OTHER INFORMATION: synthetic VRE (virus responsive element)
      derived from natural sequence

<400> SEQUENCE: 109
gggaaagcga aagtgggaaa gcgaaagtgg aaagcgaaa gtgggaaagc gaaagtg    57

<210> SEQ ID NO 110
<211> LENGTH: 97
<212> TYPE: DNA
<213> ORGANISM: Artificial sequence
<220> FEATURE:
<223> OTHER INFORMATION: minimal CMV IE promoter

<400> SEQUENCE: 110
caacaaaatg tcgtaacaac tccgccccat tgacgcaaat gggcggtagg cgtgtacggt    60
gggaggtcta tataagcaga gctcgtttag tgaaccg    97

<210> SEQ ID NO 111
<211> LENGTH: 63
<212> TYPE: DNA
<213> ORGANISM: Artificial sequence
<220> FEATURE:
<223> OTHER INFORMATION: mutant -53 promoter

<400> SEQUENCE: 111
agctttattg tcactgtccc ctgtcagtaa caactgtaat gtcactaacc cctgtctgtg    60
acc    63

MULTIPLE INTERFERON AND VIRUS RESPONSE ELEMENT CELL-BASED FLUORESCENCE SYSTEM

CROSS REFERENCE TO A RELATED APPLICATION

This application is a National Stage Application of International Application Number PCT/EP2011/002029, filed Apr. 20, 2011; which is incorporated herein by reference in its entirety.

The Sequence Listing for this application is labeled "SeqList-17Feb16-ST25.txt", which was created on Feb. 17, 2016, and is 21 KB. The entire content is incorporated herein by reference in its entirety.

The present disclosure refers to a method for a specific, versatile and sensitive detection of IFN-/virus-induced genes, a method for quantifying IFN potency and activity in a pharmaceutical preparation or biological sample, a method for distinguishing between IFN- and viral induction, and/or for distinguishing between different viruses, and a method for the quantification of virus activity. Also, the invention provides the necessary molecular tools like expression active response constructs, suitable cell lines, an array to perform the method, and a kit.

BACKGROUND OF THE INVENTION

Interferons (IFNs) belong to the class of cytokines which allow communication between cells to trigger the protective defenses of the immune system. IFNs are made and released by lymphocytes in response to the presence of pathogens like bacteria, viruses, and even tumor cells. IFN is produced and secreted by various mammalian cell lines when infected by pathogens and constitutes an important player in innate immunity against these pathogens. It also constitutes a significant therapeutic molecule in a number of viral diseases and cancers. There are hundreds of virus and IFN-stimulated genes and although their promoters harbor specific core sequences elements, they have context heterogeneity, reiterations, and different transactivation potential. These differences may account for responses to different types of IFN and viruses.

The transcription of IFN genes themselves is mediated via specific virus response elements (VRE) that bind different IFN response factors (IRF) such IRF-3 and IRF-7 in the promoters of IFN genes (Paun et al, 2007).

IFN induces the STAT/JACK pathway leading to activation and binding of transcriptional activators to the interferon-stimulated response element (ISRE) in the promoters of the IFN-stimulated genes (Sato et al., 2001; Borden et al., 2007).

There are hundreds of virus- and IFN-stimulated genes that exist in the human genome (Khabar et al., 2004) and although their promoters harbor specific core sequences elements, they have context heterogeneity, variable reiterations, and different transactivation potential. These differences may account for responses to different types of viruses, IFNs, and IRFs.

Yet, it is not possible to detect differential expression of IFN genes and IFN-stimulated genes with a versatile, simple, and sensitive method and assaying IFN bioactivity and potency is largely made with antiviral assay that requires virus propagation, virus stock maintenance, and cumbersome steps. Additionally, current gene reporter assays lack sensitivity and specificity. So, in general, the bioactivity of interferon, necessary for evaluation of therapeutic IFNs and for diagnostic purposes, is assayed customarily by a viral cytopathic effect assay or by other assays that require multiple steps such as cell destruction or dye incorporation. Certain assays utilize mRNA expression levels. The amount of transcripts of these genes can be assessed by quantitative real-time PCR of extracted mRNA. However, this method requires a large number of experimental steps, including cell lysis, RNA extraction, amplification steps which may lead to inaccurate quantification of mRNA levels. As a consequence, it may sometimes not be possible to detect differences of the expression pattern or to distinguish the trigger of the stimulation of IFN-stimulated genes, i.e. to distinguish the type of IFN or type of pathogen.

Although, there are existing reporter assays utilizing IFN-inducible promoters or standard IFN stimulated response elements, but they suffer from a lack sensitivity and selectivity.

Though the antiviral bioassay is a method of choice for titrating IFN in biological samples, this approach has been challenged with several alternatives in order to over comes these limitations. As an example, Lleonart et al (1990) developed MxA/hGH reporter assay to quantify type I IFN on Vero cells. The construct of the human growth hormone (hGH) placed under control of human IFN inducible MxA promoter which transfected into African Green monkey kidney cells (Vero cells). The production of hGH is measured by a hGH-specific radio-immunoassay (Canosi et al., 1996). However, substituted hGH gene with Luciferase gene transfected in Vero cells and the activity of Luciferase accumulated in Vero cells can be read directly after cell lysis. In recently described modified example of a reporter gene assay (Fray, Mann, and Charleston, 2001), the human Mx promoter is linked to a chloramphenicol acetyltransferase (CAT) reporter. Mx/CAT reporter was transfected into Madin-Darby Bovine Kidney (MDBK) cells and CAT expression was quantitated by commercially available ELISA. Furthermore, it was assumed that CAT reporter assay is accurate since its CAT gene is not present in eukaryotic system. This should eliminate possibility of interference to the system by indigenous proteins (Fray, Mann, and Charleston, 2001). Certain commercial reporter constructs (Stratagene, SA biosciences) are available in which tandem repeats of classical ISRE sequences (AGTTTCACTTTCCC (nucleotides 32-45 of SEQ ID NO:61)) exist of known IFN-stimulated genes, but, they lack desired sensitivity and selectivity. For example, ED50 of those constructs only ranged from 250-300 IU/m.

Thus, the object of the present disclosure is to provide a simplified and more differential approach to different types of IFN and viruses.

SUMMARY OF THE INVENTION

The object of the present disclosure is solved by the subject-matter as defined in the attached claims.

In particular, the object of the present disclosure is solved by an expression active reporter construct, comprising at least one response element, a transcriptional control element, a reporter DNA sequence, and a termination sequence, wherein the response element is an interferon-stimulated response element (ISRE) or a virus response element (VRE) comprising SEQ ID NO:1, SEQ ID NO: 2, or SEQ ID NO: 3, or any one of SEQ ID NO: 4 to SEQ ID NO: 109, or combinations of the foregoing sequences.

In one embodiment, the response element is attached to a 20-100 nucleotide region containing the response element and a flanking region. Preferably, the response element is of a length of 10-100 nucleotides. More preferably, the reporter construct has a response element that is selected of any one sequence of SEQ ID NO:4-24, or combinations of the foregoing sequences.

Preferably, the reporter construct has a transcriptional control element that comprises a minimal promoter which comprises at least a TATAA or TATAA-like signal, a GC-Box, CAAT signal, and/or an AP-1 site. In one embodiment, the minimal promoter comprises a minimal CMV promoter, a HSV TK promoter, a SV40 promoter, a synthetic minimal promoter, a viral or cellular promoter, or an inducible promoter, most preferably a minimal CMV IE promoter, in particular a minimal CMV IE promoter from position −36, −53, or 31 74 from the transcriptional start site.

The reporter protein is preferably selected from the group consisting of a luciferase, preferably Renilla and firefly luciferases, β-galactosidase, green and enhanced green fluorescent protein (EGFP), secreted alkaline phosphatase (SEAP), chloramphenicol acetyltransferase CAT), a secreted hormone, glucose oxidase, a secreted cytokine, coral reef fluorescent protein, a red and yellow fluorescent protein, and other fluorescent and bioluminescent proteins, or modifications, and destabilized forms of reporters. thereof. Most preferably, the reporter protein is an enhanced green fluorescent protein (EGFP), or an EGFP-MODC fusion protein.

The reporter construct may comprise a termination sequence that comprises a polyadenylation signal, SV40 polyadenylation, and/or, most preferably, the termination sequence is the termination sequence of bovine growth hormone (BGH).

The reporter construct may also comprise an intron or enhancer.

The object is also solved by a stable cell line expressing a reporter protein from an expression active reporter construct as described above. The cell line may be any cell line known to the skilled person, preferably a Vero, 293T, K562, MDCK, HT1080, or HepGR cell line, preferably a liver cell line most preferably a Huh-7 cell line.

The object is also solved by an array comprising at least one expression active response reporter construct, wherein the expression active response reporter construct comprises a response element, a transcriptional control element, a reporter DNA sequence, and a termination sequence, wherein the response element is an interferon-stimulated response element (ISRE) or a virus response element (VRE), or combinations thereof.

Preferably, the expression active reporter construct is one as described above. Preferably, the array comprises at least one expression active reporter construct, wherein the sequence of the response element of the reporter construct is selected from SEQ ID NO: 4 to SEQ ID NO: 109, preferably from SEQ ID NO: 4 to SEQ ID NO: 24.

Preferably, the array comprises at least two expression active reporter constructs as described above, wherein at least two reporter constructs have different response elements, and wherein the sequences of the response elements are selected from SEQ ID NO: 4 to SEQ ID NO: 109. More preferably, the sequences of the response elements are selected from SEQ ID NO: 4 to SEQ ID NO: 24.

More preferably, the array comprises at least thirteen expression active reporter constructs as described above, wherein at least two reporter constructs have different response elements, and wherein the sequences of the response elements are selected from SEQ ID NO: 4 to SEQ ID NO: 109. Most preferably, the array comprises at least thirteen different expression active reporter constructs, wherein at least thirteen reporter constructs have different response elements, and wherein the sequences of the response elements are selected from SEQ ID NO: 4 to SEQ ID NO: 24.

In a preferred embodiment, the array comprises reporter constructs with response elements that comprise at least two different sequences selected from SEQ ID NO: 4, SEQ ID NO:5, SEQ ID NO: 6, SEQ ID NO: 7, SEQ ID NO: 8, SEQ ID NO: 9, SEQ ID NO: 10, and SEQ ID NO: 11. More preferably, the sequences are selected from SEQ ID NO: 12, SEQ ID NO: 13, SEQ ID NO: 14, and SEQ ID NO: 58.

In a preferred embodiment, the array comprises reporter constructs with response elements that comprise at least two different sequences selected from SEQ ID NO: 4, SEQ ID NO:5, SEQ ID NO: 6, SEQ ID NO: 7, SEQ ID NO: 8, SEQ ID NO: 9, SEQ ID NO: 10, and SEQ ID NO: 11. More preferably, the sequences are selected from SEQ ID NO: 12, SEQ ID NO: 13, and SEQ ID NO: 14.

In a preferred embodiment, the array comprises reporter constructs with response elements that comprise SEQ ID NO: 4 (VREL-1), SEQ ID NO: 11 (PARP10), SEQ ID NO: 16 (OAS3V2), and SEQ ID NO: 9 (USB18-M).

In yet another preferred embodiment, the array comprises reporter constructs with response elements that comprise SEQ ID NO: 16 (OAS3V2), SEQ ID NO: 10 (IFIT3-2), SEQ ID NO: 4 (VREL-1), SEQ ID NO: 53 (GIP3-6-16), SEQ ID NO: 5 (VREL-2), SEQ ID NO: 12 (IFIT3-1), SEQ ID NO: 78 (GPB1-V), SEQ ID NO: 14 (VRE Con), SEQ ID NO: 58 (AB VRE), SEQ ID NO: 62 (IFNA-V), SEQ ID NO: 33 (MX-1), SEQ ID NO: 15 (OAS3-V), and SEQ ID NO: 11 (PARP 10).

In yet another preferred embodiment, the array comprises reporter constructs with response elements that comprise SEQ ID NO:104 (AB-VRE-M2), SEQ ID NO: 5 (VREL-2), SEQ ID NO: 4 (VREL-1), SEQ ID NO: 100 (VRE-G1), SEQ ID NO: 9 (USB18-M), SEQ ID NO: 101 (SYN-ISRE-2R), SEQ ID NO: 19 (PARP10-S), SEQ ID NO: 11 (PARP10), SEQ ID NO: 16 (OAS3V2), SEQ ID NO: 15 (OAS3-V), SEQ ID NO: 18 (MX1-2-2), SEQ ID NO: 33 (MX1), SEQ ID NO: 62 (IFNA-V), SEQ ID NO: 23 (IFIT3-2S), SEQ ID NO: 10 (IFIT3-2), SEQ ID NO: 12 (IFIT3-1), SEQ ID NO: 24 (IFIT1), SEQ ID NO: 78 (GPB1-V), SEQ ID NO: 53 (GIP3-6-16), SEQ ID NO: 105 (AB-VRE-M), SEQ ID NO: 58 (AB-VRE), SEQ ID NO: 31 (HERC5), SEQ ID NO: 102 (SYN-ISRE-2), SEQ ID NO: 103 (B-VRE-3×), and SEQ ID NO: 74 (PSMP9-V).

Optionally, the selection of sequences also comprises SEQ ID NO: 58.

The object is also solved by any responsive element that comprises a sequence that comprises more than one repeat derived from natural VRE/ISRE context, for example PARP10S and IFIT3-2S (see SEQ ID NO. 19, and 23). Also, the responsive element may comprise a sequence that is complementary to any of the sequences mentioned above, a transcript of one of the sequences, or a sequence that hybridizes to any of the sequences mentioned above under stringent conditions.

Also, the array may comprise an expression active reporter construct that is transfected into a stable cell line as described above.

The object is also solved by a kit comprising an array as described above, a buffer, and optionally a stable cell line, preferably also comprising an instruction sheet.

The object is further solved by a method for detection of IFN- and/or viral induction, comprising the steps of providing an array with expression active reporter constructs as described above, the transfection of the expression active reporter constructs into cells, and exposing cells to conditions suspected of being characterized by the presence of IFN and/or a virus, and detection of reporter activity. Preferably, the detection of reporter activity is indicative of the presence of IFN and/or a virus.

The object is further solved by a method for quantifying IFN potency and activity in pharmaceutical preparation or biological samples, comprising the steps of providing an array with expression active reporter constructs as described above, the transfection of the expression active reporter constructs into cells, and exposing cells to conditions suspected of the IFN formulation to be quantified and detection of reporter activity.

The object is also solved by a method for distinguishing between IFN- and viral induction and/or distinguishing of different viruses, comprising the steps of providing an array with expression active reporter constructs as described above, transfection of the expression active reporter constructs into cells, and exposing cells to conditions suspected of being characterized by the presence of IFN and/or a virus, and detection of reporter activity. Preferably, a detection of reporter activity is indicative of the presence of IFN and/or a virus.

The object is further solved by a method for quantification of virus activity comprising the steps of providing an array with expression active reporter constructs as described above, the transfection of the expression active reporter constructs into cells, and exposing cells to conditions suspected the virus stock to be quantified and detection of reporter activity.

The conditions of the methods of the invention can be conditions where the reporter constructs or transfected cells are exposed to recombinant (r) IFNs including therapeutic/pharmaceutical IFN formulations such as, but not limited to, rIFN-α2a, rIFN-α2b, pegylated IFN, albuferon, abd IFN-beta-serine, IFN-con1, or any other IFN source or IFN containing formulation, or wherein the reporter constructs or transfected cells are exposed to any virus or virus containing formulation. Also, the reporter constructs or tranfected cells may be exposed to biological samples such as cell culture medium, serum, plasma, patient serum, that may contain IFN or virus or both, or virus stocks, purified or non-purified, which may induce IFN.

In a preferred embodiment, the object is solved by said methods, wherein the array and the reporter construct are any one as described above. In yet another embodiment, the reporter construct is in a 96-well plate or a 384-well plate. In another preferred embodiment, the cell line used in the described method is any one as described above. In yet another preferred embodiment, the detection method is selected of Western blotting, colorimetric method, fluorescence, luminescence, or biosensors.

The object is also solved by the expression active reporter construct, the cell line, the array, and the method, or the kit as described above for use in viral detection assays. Preferably, the expression active reporter construct, the cell line, the array, and the method, or the kit is used for detection assays for Herpes simplex virus (HSV), EMC virus (EMCV), Vesicular stomatitis virus (VSV), influenza virus (FluV), Newcastle disease virus (NDV), hepatisic A, B, or C viruses, RNA viruses, DNA viruses, viral RNA, viral DNA, microbial DNA, microbial RNA, and/or respiratory syncytial virus (RSV).

DESCRIPTION OF THE PREFERRED EMBODIMENTS OF THE INVENTION

It is to be understood that this invention is not limited to the particular methodology, protocols and reagents described herein as these may vary. Also, the terminology used herein is for the purpose of describing particular embodiments only, and is not intended to limit the scope of the present disclosure which will be limited only by the appended claims. All technical and scientific terms used herein have the same meanings as commonly understood by one of ordinary skill in the art, unless described otherwise. For the purpose of the present invention, all references cited herein are incorporated by reference in their entireties.

The principle advantage of the invention is that molecular tools for quick and simple differentiation of various triggers of the IFN cascade are provided. The invention provides reporter constructs, cell lines, an array, a kit and a method for a more sensitive and versatile detection of IFN triggers and their differentiation.

The described reporter gene approach, i.e. introducing an IFN- or virus-responsive element or modification thereof, and a transcriptional control in a reporter construct, combining such constructs in a biological array, and detecting fluorescence of these constructs upon induction with IFN or virus is simple, versatile and adaptable to high throughput studies that are important in both academic and pharmaceutical research and development activities including drug discovery processes. The invention can be used with any different applications in the field of life sciences including, but not limited to, drug screening, drug target screening, research tool in molecular and cell biology, personalized medicine, pharmacogenomics, and correlation of genetic variations and polymorphisms with phenotypic outcomes.

Reliable IFN assay for determination of IFN concentration in biological samples is a key success of therapeutic response and in patient management. Although the available immunoassays are sensitive and specific they do not differentiate between biologically active and inactive IFN. In contrast, antiviral assays distinguish biological activity but lack sensitivity and required the maintenance of permissive cell lines and viral stocks. Viral inhibition assay using several reference virus and cell lines is routinely used assay to quantify the inhibition activities on viral propagation and replication (Khabar et al., 1996). Biological assay of IFN required defined reference IFN preparation and reproducible bioassay. Thus, reporter bioassays that are driven by a strong and specific IFN-inducible sequences is advantageous. These reporter constructs, cell lines, and assays will be used to evaluate human recombinant IFN therapeutics and to measure IFN activity in biological samples. In contrast to virus inhibition assay, the reporter assay constitutes simple, selective and reliable assay that allow no virus or secondary assays.

The invention enables the detection and differentiation of IFN, Herpes simplex virus (HSV), EMC virus (EMCV), Vesicular stomatitis virus (VSV), influenza virus (FluV), Newcastle disease virus (NDV), and/or respiratory syncytial virus (RSV). Also, hepatisic A, B, or C viruses, RNA viruses, DNA viruses, viral RNA, viral DNA, microbial DNA, microbial RNA may be detected.

The invention encompasses the following methods:
1. A method for detecting IFN and/or viral induction,
2. a method for quantifying IFN potency and activity in pharmaceutical preparation or biological samples,
3. a method for distinguishing between IFN- and viral induction, and/or for distinguishing between different viruses, and
4. a method for the quantification of virus activity.

1. Methods of the Invention

The method disclosed herein comprises the steps of assessing an IFN/VRE-responsive reporter construct, transfecting a cell line with the reporter constructs, and imaging the transcription activity of the reporter element.

The principle advantage of this method is that this method is a simple, versatile, and sensitive molecular tool for IFN/virus detection and differentiation and quantification.

The multiple IFN and virus sensing reporter system is a reporter assay that is functionally effective, simpler, and accurate in monitoring and quantifying IFN and IFN stimuli, e.g., viruses and viral products, in biological systems. It utilizes potent sequences elements chosen from IFN stimulated genes that comprise not only ISRE and VRE but also ISRE-like and VRE-like along with context sequence regions. These results in more potent responses, earlier responses, and selective responses. In addition, the use of more than one ISRE/VRE construct can allow further selective responses to IFN triggers and IFN types.

Conditions suspected of being characterized by the presence of IFN and/or a virus, conditions suspected of the IFN formulation to be quantified, conditions suspected of being characterized by the presence of IFN and/or a virus, and conditions suspected the virus stock to be quantified may include all conditions where the reporter constructs or transfected cells are exposed to recombinant (r) IFNs including therapeutic/pharmaceutical IFN formulations such as, but not limited to, rIFN-α2a, rIFN-α2b, pegylated IFN, albuferon, abd IFN-beta-serine, IFN-con1, or any other IFN source or IFN containing formulation, or wherein the reporter constructs or transfected cells are exposed to any virus or virus containing formulation. Also, the reporter constructs or transfected cells may be exposed to biological samples such as cell culture medium, serum, plasma, patient serum, that may contain IFN or virus or both, or virus stocks, purified or non-purified, which may induce IFN.

2. Expression Active Response Reporter Constructs

The present disclosure is versatile in that it can be used with any minimal promoter, a portion of a promoter, an enhancer, positive or negative cis-acting sequences, inducible or repressible control element, and 5' UTR sequences that are upstream of the gene, or a reporter. An example of a minimal promoter is the CMV minimal promoter which contains an SP1 site (reversed), CAAT (reversed), GC box, and TATA signal. Another example is the SV40 minimal promoter, Moloney murine leukemia virus promoter (LASN), and HSV-1 TK minimal promoter which contains CCAAT (inverted), SP1, GC-box, and TATA signal. Strong promoters can be derived from housekeeping genes that are abundant, for example, but not limited to, eukaryotic elongation factor alpha (EEF1A1), actin gamma, actin beta, GAPDH, ribosomal proteins, etc. Any minimal promoter can be derived from any strong promoter.

In a preferred example, the minimal promoter is a minimal CMV IE promoter, in particular a minimal CMV IE promoter from position −36, −53, or −74 from the transcriptional start site (FIG. 2, Example 3). Most preferably, the minimal promoter is a minimal CMV IE promoter from position -74 from the transcriptional start site The use of a minimal promoter results in a high induction and accordingly enhances sensitivity of the reporter construct.

The reporter construct were further assessed by using a responsive element with the minimal promoter (FIG. 2). For this purpose, a variety of natural and artificial ISRE or VRE elements may be used. VRE- and ISRE containing promoters that are responsive to IFN have been searched by a first gene expression profiling (see Example 2). The candidate gene cluster comprised the gene cluster as described in Table 1 (see below). Preferred sequences of the response elements as disclosed herein are:

SEQ ID NO: 4
GGGAAACCGAAACTGGGGAAACCGAAACTGGGGAAACC
GAAACTGGGAAACCGAAAC

SEQ ID NO: 5
GGAAACCGAAAGGGGAAAGTGAAACTAAAGCTGAAACC
GAAAGGGGAAAGTGAAACTAAAGC

SEQ ID NO: 6
GGGAAAATGAAACTCGGAGCTGGGAGAGAGGGGAAAAT
GAAACTGCAGAAATAGAA

SEQ ID NO: 7
GCTAGGTTTCGTTTCTGCGCCCCACAGGGTCTGTGAGT
TTCATTTCTTC

SEQ ID NO: 8
TGAGTTTCGTTTCTGAGCTCCTTTCATTTTCACCGGTT
TCAATTCTCCTCTGGA

SEQ ID NO: 9
CTCCCGGCGCGGAGGCCGCTGTAAGTTTCGCTTTCCATT
CAGTGGAAAACGAAA

SEQ ID NO: 10
GATTCTGTTTCAGTTTCCCCTCAAGAGGGATCTTGATAG
GGTTCCATCAGTTTCACTTTCCTTTCCCCTTTCATCC

SEQ ID NO: 11
CCTCCTTCCGTCTTTCAGTTTCACTTTTGTTTTCCTGCT
CCTGCTCCCTC

SEQ ID NO: 12
GTTTCATTTTCCTCCTCCCAACGATTTTAAATTAGTTT
CACTTTCCAGTTTCCTCTTCCTT

SEQ ID NO: 13
AAAAAACTGAAACTCAGCCTGAAAGATGAACAGAACAA
AACAGAAATCCT

SEQ ID NO: 14
GAAAGTGAAAAGAGAAATGGAAAGTGGAAAAGGAGAAA
CT

SEQ ID NO: 15
AGTGTCTGATTTGCAAAAGGAAAGTGCAAAGACAGCTC
CT CCCTTCTGAGG

SEQ ID NO: 16
TTCGGAGAGCCGGGCGGGAAAACGAAACCAGAAATCCG
AAGGCCGCGCCAG

SEQ ID NO: 17
GCTAGGTTTCGTTTCTGCGCCCCACAGGGTCTGTGAGT
TTCATTTCTTCGCG

SEQ ID NO: 18
TGAGTTTCGTTTCTGAGCTCCTTTCATTTTCACCGGTT
TCAATTCTCCTCTGGAG

SEQ ID NO: 19
CTCCTTCCGTCTTTCAGTTTCACTTTTGTTTTCCTGCT
CAGTTTCACTTTTGTTTT

SEQ ID NO: 20
CAGCTTCAGTTTTCCTAATGACAGTGAGTCATTTCTTC
TCTCTCTTTT

SEQ ID NO: 21
CCATTTCCCTCCCTCCTCTCATAGACAACCGATATATA
TCTTTCACTTTGGTG

SEQ ID NO: 22
GTTTCATTTTCCTCCTCCCAACGATTTTAAATTAGTTT
CACTTTCCAGTTTCCTCTTCCTT

SEQ ID NO: 23
GATTCTGTTTCAGTTTCCCCTCAAGAGGGATCTTGATA
GGGTTCCATCAGTTTCACTTTCCTTTCCCCTTTCAT

```
                                          SEQ ID NO: 24
TCCGCTAGCTTTAGTTTCACTTTCCCCTTTCGGTTTCC
CTAGGTTTCCAACTTG
                                          SEQ ID NO: 25
AGTCCTGCCAATTTCACTTTCTAGTTTCACTTTCCCTT
TTGTAACGTCAGCTG
                                          SEQ ID NO: 26
CCTTCTCTTTCCCTTTCCAGCACTTTGATTCCTTGTGG
TGTCTGTTTCTGTTTTGTTAGTAATTTCATG
                                          SEQ ID NO: 27
ATCTCCATCAAACCAAGATCCTAAGGGCTGGAAGTTTG
TCTTTTCCATCATTG
                                          SEQ ID NO: 28
AAAGTTTGACTTTCTCTGCACAGTTCCACTTTCAGAGT
TTTGCTTTTGTTG
                                          SEQ ID NO: 29
TCTCATTTTCATTTTTACCTGTTTTGTCTTACTTTGTA
CTTTACCCAGTTTCGCTTTATCATCTG
                                          SEQ ID NO: 30
GATGATCTTTCCACTTCCTGGTTTTTCTGACTTTTTTT
CTTTTTGCAGTG
                                          SEQ ID NO: 31
GTTTCCTTTTCCTTTTCGATTCCGCCCCCTAACATTAT
GTTTCGTTTTCCACTG
                                          SEQ ID NO: 32
CCAGCTCCCGGCGCGGAGGCCGCTGTAAGTTTCGCTTT
CCATTCAGTGGAG
                                          SEQ ID NO: 33
GCTAGGTTTCGTTTCTGCGCCCCACAGGGTCTGTGAGT
TTCATTTCTTCGCG
                                          SEQ ID NO: 34
TGAGTTTCGTTTCTGAGCTCCTTTCATTTTCACCGGTT
TCAATTCTCCTCTGGAG
                                          SEQ ID NO: 35
GGGCTGGGCACACTGAGTTTCAGTTTCCTTTCTCTGAG
TCTTTGAAGCTTCG
                                          SEQ ID NO: 36
GGTAAATGTCTTTCTGCTTTTCATTTTTCCTAGCTAGC
ATTAGTCTCTCTG
                                          SEQ ID NO: 37
CCGCTAGTTGCACTTTCGATTTTCCCTTTAGTTATTAA
AG TTCCTATGCAG
                                          SEQ ID NO: 38
AGTCCCCGCCACTTTTGCTTTTCCCTGTCTTTCGGTCA
TTCGGTTTTGTTTCTTCCG
                                          SEQ ID NO: 39
GCTGCCTTTTCTCCTGCCGGGTAGTTTCGCTTTCCTGC
GCAGAGTCTGCGGAG
                                          SEQ ID NO: 40
CCTCCTTCCGTCTTTCAGTTTCACTTTGTTTTCCTGC
TCCTGCTCCCTCG
                                          SEQ ID NO: 41
AATTCGCTTTCCTTTTCTGTTTCCCGCGGTGTCCTTAA
CCAAAGGCCTCCTCTCTTCA
                                          SEQ ID NO: 42
TGATATCTTATTGTGGTTTTGCTTTGCATTTCCCTGTGA
GCACCTTTTCATATG
                                          SEQ ID NO: 43
CACTTCTTTCAAAGTGGTTTCTTTCAGTTTTCCTATTAA
GTTCCTGTGTTGCTTCTTG
                                          SEQ ID NO: 44
AGTTTTCTGTCATAATTTCTTTTCTACCCTTTTCTCTTT
GCTCCTTCTGAGACA
                                          SEQ ID NO: 45
CCATTCTTTTATTCCTTTACCTTTGCTTTCACTTTACTC
TACCCTTAATTCTTTCTTG
                                          SEQ ID NO: 46
ACTCTTTGCTATTTAGTTTCATTTTTGTTTTAAGTTTCA
CTTTGCAGCTGTTTCTTTTT
                                          SEQ ID NO: 47
AGGTTCCTCTTTTCTTTCCAGAGCCAGTTGACAGATTTA
CCTTCTCTTTAAG
                                          SEQ ID NO: 48
ACAGTTTTAGCTTTACAATTTTTTTTCTCTTTCCTTTTG
TTGTGAATTCATTTACCTAACG
                                          SEQ ID NO: 49
ATTTGACTTCCTCTTTTCCTAACTGAATACTCTTTATTT
CTTTATCCTGCCTAAGAACTT
                                          SEQ ID NO: 50
CAATTTCACTTTTATTCCTCTTTCTTCTCCTTACCTATT
TTTGACACATTTATTCAGTATG
                                          SEQ ID NO: 51
CTGTGGCTTTCGCTTTCACTTCCTCCTCTTTCGCTTTCA
CTTCCTCC CCGAGAG
                                          SEQ ID NO: 52
AGCTTTAGTTTCACTTTCCCCTTTCGGTTTCAGCTTTAG
TTTCACTTTCCCCTTTCGGTTTCCG
                                          SEQ ID NO: 53
GGGAAAATGAAACTCGGAGCTGGGAGAGAGGGGAAAATG
AAACTGCAGAAATAGAAACTG
                                          SEQ ID NO: 54
AAGTAAAGAAAGTGAAAGTGAAAAGGAGATTGGAAAGCA
AGGAAAGGAGAAACG
                                          SEQ ID NO: 55
GAAAGTGAAAGTGAAAGTGAAAGTGAAAGTGAAAGTGAA
AGTG
                                          SEQ ID NO: 56
GAAAGTGAAAAGAGAATTGGAAAGCGAAAGTGAAAAGAG
AATTGGAAAGCG
                                          SEQ ID NO: 57
AAGTGAAAGTGAAAGTGAAAGTGAAAGTGAAAGTGAAAG
TGAAAGTG
                                          SEQ ID NO: 58
AGAAATGGAAAGTAGAAATGGAAAGTGAGAAGTGAAAGT
GAGAAGTGAAAGTG
                                          SEQ ID NO: 59
GGGAAAGAGAAACCGGAAAAGCGAAACTGGAAAGAGAAA
CCGGAAAAGCGAAACTG
                                          SEQ ID NO: 60
ACTTTTGCTTTTCCCTGTCTTTCGGTCATTCGGTTTTGT
TTCTTCCGGGAAAGGGAAACCGAAACTGAAG
                                          SEQ ID NO: 61
AAGAAAAAGAGTCCTGCCAATTTCACTTTCTAGTTTCAC
TTTCCCTTTTGTTGAAGGGAAACAAACAAAAAGGAA
                                          SEQ ID NO: 62
GAGAAACATAAAGAGTGCATGAAGGAAAGCAAAAACAGA
AATGGAAAGTGGCCCATTAAGAAAGTGGAAATCAG
                                          SEQ ID NO: 63
CACAAATGAAAACAGTAAAAGAAACTGAAAGTACAGAGA
AATGTTCAGAAAATGAAAACCATGTGT
```

SEQ ID NO: 64
TAGAAAGAGCATAAAAGAAAGCAAAAAGAGAAGTAGAAA
GTAGGCAAGAAAATGGAAACTGTGACCTTG

SEQ ID NO: 65
CAGCAAAGTGGAACTTAAGAGGGGAAGTGAAACAGGGAA
ATGCAAGGAGAAAGGCGAAAG

SEQ ID NO: 66
CTGAAAGATGACTCAGTTAAGAAGCTGGAAAATAAAACC
AGGTCTTATTCTGAACTGAAAGTC

SEQ ID NO: 67
AGATGGGCACTGTTTCTTATCCCAATTTTACAGATGGGA
AAACTGAAGCTCAGGGAGGCAAG

SEQ ID NO: 68
AGTAGAAAAGAGCAAGTCTAAGGAATATCTAGAAAAGAG
GAAGTTAGAACCATAGAAAAGG

SEQ ID NO: 69
TGAATTATTTCTCCTCCTTCAATTTCAGTTTGCTCATAC
TTTGTGACTTGCGGTCACAGTG

SEQ ID NO: 70
ATGAGGGGAGAAAGATGTCTGCAGTTTCGGTTTCCTGGA
AAATGAAACCTGG

SEQ ID NO: 71
AGTGTCTGATTTGCAAAAGGAAAGTGCAAAGACAGCTCC
TCCCTTCTGAGG

SEQ ID NO: 72
TGTAAATGGAAAAACGAAATGACAAATAATTATGAAAGA
GGCATCCATTTG

SEQ ID NO: 73
TGAGCAGGCGGCCGCTTTCGATTTCGCTTTCCCCTAAAT
GGCTGAGCTTG

SEQ ID NO: 74
CAGCCATTTAGGGGAAAGCGAAATCGAAAGCGGCCGCCT
GG

SEQ ID NO: 75
ACAGCAGGAAATAGAAACTTAAGAGAAATACACACTTCT
GAGAAACTGAAACGACG

SEQ ID NO: 76
TGCCTCGGGAAAGGGAAACCGAAACTGAAGCCAAATTTG
GCCAG

SEQ ID NO: 77
TGTAACG TCAGCTGAAGGGAAACAAAC AAAAAGGAAC
CAGAGGCCACG

SEQ ID NO: 78
AAAAAACTGAAACTCAGCCTGAAAGATGAACAGAACAAA
ACAGAAATCCTG

SEQ ID NO: 79
ACACGGTTATAGACAAAGAAAAAACTGAAACCCAGCATC
AAAGAGGAACAG

SEQ ID NO: 80
TACAAAATGGAAAAACAGAACAAAACAGAAAACCTAAAG
CTGTATTGCTGG

SEQ ID NO: 81
AGTAGTAAGTTTTGCTTTACAAATTCTTACATTGCAGAAT
CGTCTGCATCAGCTAG

SEQ ID NO: 82
CGCCAGCGCGGGAACCGGGAAAAGGAAACCGTGTTGTGTA
CGTAAGATTCG

SEQ ID NO: 83
GCTGCTAGAAAGAAACGAAACTGAAAGCAGGGAATG

SEQ ID NO: 84
CTTTGTAGGTTTTTGTTTTCTTTTGATTTCAGTTTCCATTT
CCTCTG

SEQ ID NO: 85
GTTAAATACTTTCACTTCTCTTTTCCCCATTTGGGCGGAGC
CCTTTCTGAGTCAGTCG

SEQ ID NO: 86
TGCAGGGAAGTACCGGGAAGGACTTTCCAGCGCAGGGAGTTT
CTCCGCTTGGAAATTCCCCGG

SEQ ID NO: 87
GTAACAAAAGCGAAACTCCATCTCAAAAAAGAAACGCAAGG

SEQ ID NO: 88
AAATGTAAATGACATAGGAAAACTGAAAGGGAGAAGTGAAAG
TGGGAAATTCCTCTGAATG

SEQ ID NO: 89
CTAAAATGTAAATGACATAGGAAAACTGAAAGGGAGAAGTGAA
AGTGGGAAATTCCTCT

SEQ ID NO: 90
TGCTATTATGAAGGAAAAAGTGAAATGGAAATTAAAAAC

SEQ ID NO: 91
CTCGGGAAAGGGAAACCGAAACTGAAGCC

SEQ ID NO: 92
AGCCTGATTTCCCCGAAATGACGGCAGCCTGATTTCCCCGAAA
TGACG

SEQ ID NO: 93
TTTCAGAAACAGTTCATGTTTTGGAAAGTGAAACCTAATTCACT
ATTACCAAAAAAGAGGAGCAGAGG

SEQ ID NO: 94
TGATGTTTTCATTCAGGGACTTGAAACTTGTTTTAACACATGAG
CAATGTTTTCCCTCAAAATAG

SEQ ID NO: 95
AAGGCCCTCCCTGGAGGAGAACTGAAACTTAGGGTGGGGACTGT
AGAAAG

SEQ ID NO: 96
AGGGCGGCGCAGGGCGGCGCTTCTCGGAAAGCGAAAGCCGGCGG
GGCG

SEQ ID NO: 97
CTTCTGAGTCTTAGAGAAAAAGGAACTGGAGCCCCAGACC

SEQ ID NO: 98
AACACATGTAGAGAGTGCAAAAAGAAAGCAAAAACAGACATAGAA
AGTAA

SEQ ID NO: 99
GAGTGCATGAAGGAAAGCAAAAACAGAAATGGAAAGTGGCCCAGAA

SEQ ID NO: 100
GGGAAACCGAAAGTGGGAAACCGAAAGTGGGAAACCGAAAGTGGGA
AACCGAAAGTG

SEQ ID NO: 101
TACTTTCGCTTTCCACTTTCGCTTTCCTCACTTTCGCTTTCCTACT
TTCGCTTT

SEQ ID NO: 102
GGGAAACCGAAACTAGGAAACCGAAACTGAGGAAACCGAAACTGGA
AACCGAAACTA

SEQ ID NO: 103
GAGAAGTGAAAGTGAGAAGTGAAAGTGAGAAGTGAAAGTG

SEQ ID NO: 104
AGAAATGGAAAGTGAGAAGTGAAAGTAGAAATGGAAAGTGAGAAGT
GAAAGTG

-continued

SEQ ID NO: 105
AGAAATGGAAAGTAGAAATGGAAAGTACTGCGAGAAGTGAAAGTGAG
AAGTGAAAGT

SEQ ID NO: 106
AGTGTCTGATTTGCAAAAGGAAAGTGCAAAGACAGCTCCTCCCTTCT
GAGG

SEQ ID NO: 107
GCTGCTAGAAAGAAACGAAACTGAAAGCAGGGAATG

SEQ ID NO: 108
GGGAAACCGAAAGTAGGAAACCGAAAGTGAGGAAACCGAAAGTGGAAAC
CGAAAGTA

SEQ ID NO: 109
GGGAAAGCGAAAGTGGGAAAGCGAAAGTGGGAAAGCGAAAGTGGGAAAG
CGAAAGTG

This allowed identifying a consensus region of GAAANNGAAASY (SEQ ID NO:1), wherein S is G or C, and Y is T/U or C, and N is A, G; C, or T/U; or GAAAANNGAAASY (SEQ ID NO:2), wherein S is G or C, and Y is T/U or C, and N is A, G, C, or T/U; or RNGAAANNGAAACT (SEQ ID NO:3), wherein R is A or G, and N is A, G, C, or T/U.
with the core region AANNGAAA. In a further selection, 58 strongly induced (6 fold) gene cluster (FIG. 1, Table 1) can be determined. These preferred sequences are the gene clusters of ARF1, C10orf118 (SEQ ID NO:81), C3, CASP7 (SEQ ID NO: 42-45), CXCL10, DDX58 (SEQ ID NO: 37), EPSTI1 (SEQ ID NO: 90), G1P2, G1P3, GBP1 (SEQ ID NO: 12), GBP3, HERC5 (SEQ ID NO: 31), IFI27, IFI44 (SEQ ID NO:35), IFIH1 (SEQ ID NO:41), IFIT1 (SEQ ID NO:24), IFIT2 (SEQ ID NO:61, 83), IFIT3 (SEQ ID NO:10, 12, 22, 23), IFIT5, IFITM1 (SEQ ID NO: 75), IRF1, ISG15 (SEQ ID NO: 38, SEQ ID NO: 82), ISG20, ISGF3G, LAP3, MATR3 (SEQ ID NO: 27 to 29), MT2A, MX1 (SEQ ID NO: 33, 6, 7, 17, 18, 34), MYD88 (SEQ ID NO: 102), NPIP, NT5C3 (SEQ ID NO: 46, 47, 48), OAS1 (SEQ ID NO: 30), OAS2, OAS3 (SEQ ID NO:89), OASL, P4HB, PARP10 (SEQ ID NO: 11, 40), PLSCR1 (SEQ ID NO:82), PPIA, PRIC285, PSMB8, PSMB9, PSMD1, PSME1, SAMD9, SELPLG (SEQ ID NO: 67), SLC15A3, SP100 (SEQ ID NO:85), STAT1 (SEQ ID NO:39), STAT2, TAP1 (SEQ ID NO:73), TMEM67 (SEQ ID NO:26, SEQ ID NO: 72), TRIM22, UBE2L6, USP18 (SEQ ID NO:32).

Accordingly, the invention discloses selected ISRE and VRE sequences that are more superior than traditional reporter assays in response to IFN and/or virus. Also, the inventions describes the use of more than one ISRE or VRE, as in combination of two or more they yield more information such as distinction between IFN and virus, or as a pattern to distinguish between IFN stimuli.

The inventions describes the use of more than one ISRE or VRE, as in combination of two or more they yield more information such as distinction between IFN and virus, or as a pattern to distinguish between IFN stimuli.

Certain commercial reporter constructs (Stratagene, SA biosciences) are available in which tandem repeats of classical ISRE sequences (AGTTTCACTTTCCC) (nucleotides 32-45 of SEQ ID NO:61) exist of known IFN-stimulated genes, but, they lack desired sensitivity and selectivity. For example, ED50 of those constructs ranged from 250-300 IU/m. In contrast, the ED50 of the constructs of the invention is near 10 IU/ml, thus, are more sensitive. Especially those sequences toward the top of the list in Table 3, in particular SEQ ID NO: 53, SEQ ID NO: 19, SEQ ID NO: 33, SEQ ID NO: 34, SEQ ID NO: 4, SEQ ID NO: 9, SEQ ID NO: 5, SEQ ID NO: 75, SEQ ID NO: 83, SEQ ID NO: 24, SEQ ID NO: 100, SEQ ID NO: 10, SEQ ID NO: 108, SEQ ID NO: 11, SEQ ID NO: 70, SEQ ID NO: 23, SEQ ID NO: 109, SEQ ID NO: 60.

The responsive element can also comprise an artificial modification of a sequence or repeats of VREs/ISREs. Artificial sequences of the invention can be derived from natural sequences. Artificial sequences are in particular VREL1 (SEQ ID NO:4), VREL2 (SEQ ID NO:5), USB18-M (SEQ ID NO:9), VRE-Con (SEQ ID NO:14), PARP10-S (SEQ ID NO:19), IFIT3-2S (SEQ ID NO: 23), ISRE-74 (SEQ ID NO:52), 7XVRE1 (SEQ ID NO:55), PRD2X (SEQ ID NO:56), 7VRE2 (SEQ ID NO:57), AB-VRE (SEQ ID NO:58), VREL-3 (SEQ ID NO:59), ISG15-M (SEQ ID NO:60), IFIT2-M (SEQ ID NO:61), SELPLG-M (SEQ ID NO: 67), VRE-G1 (SEQ ID NO:100), SynISRE-2R (SEQ ID NO:101), SynISRE-2 (SEQ ID NO:102), B-VRE-3X (SEQ ID NO:103), AB-VRE-M2 (SEQ ID NO: 104), AB-VRE-M (SEQ ID NO: 105), SYN-VRE-1 (SEQ ID NO:108), VRE-G2 (SEQ ID NO:109). The artificial sequences are synthetic VRE (virus responsive element) or ISRE (IFN stimulated responsive element) derived from natural sequences (i.e. modified from sequences from natural ISRE/VRE).

In the examples enclosed herein, a C-terminal modified EGFP-MODC reporter was used as an example. When particularly applied with advanced imaging processing, it is sensitive and has a large dynamic range. The benefit of earlier response is to allow flexibility in assay development and alternative drug screening approaches. Such assay can be performed on living cells allowing repeated monitoring without cell lysis and other manipulating resulting in intra-well variance. Other possible reporter are selected from the group consisting of a luciferase, preferably Renilla and firefly luciferases, β-galactosidase, green and enhanced green fluorescent protein (EGFP), secreted alkaline phosphatase (SEAP), chloramphenicol acetyltransferase CAT), a secreted hormone, glucose oxidase, a secreted cytokine, coral reef fluorescent protein, a red and yellow fluorescent protein, and other fluorescent and bioluminescent proteins, or modifications thereof. Most preferably, the reporter protein is an enhanced green fluorescent protein (EGFP).

The transcriptional activity due to the reporter or the gene of interest can also be assayed using the mRNA levels. Real time RT-PCR, Northern, RNase protection assay, or any other mRNA or RNA detection and measurement method can be used. Alternatively, protein levels can be assayed when secreted using ELISA or other means as in the case of secreted SEAP and β-galactosidase or by Western blotting as in the case of GFP or other intracellular proteins.

The use of the MODC C-terminus amino acids to destabilize the GFP protein contributed to better and earlier response (e.g., four to six hours, FIG. 4) to IFN since MODC contains the protein instability determinants, PEST, known to occur in many proteins with short half life (Li et al., 1998).

The benefit of an earlier response is to allow flexibility in assay development and alternative drug screening approaches. FIG. 5 shows the excellent linear dynamic response of such reporter constructs.

The termination sequence preferably comprises an eukaroytic polyadenylation signal, pol III termination signal, thymidines stretch, U1 termination signal, pol I termination signal, or synthetic termination variant. Throughout this application, the designation termination shall apply to the above eukaryotic signals in the embodiments.

The method to generate the reporter constructs utilizes the use of the reporter, preferably destabilized EGFP plasmid as previously described (al-Haj et al., 2009) and ISRE/VRE sequences containing primers. The expression active PCR products are generated directly from the reporter vector using two primers, a forward primer at the 3'end which targets a minimal promoter region of the minimal promoter upstream of the EGFP coding region, and the putative IFN/ISRE sequence context region. The reverse primer contains a complementary sequence to the downstream region of the poly (A) site. The forward primer preferably contains 18 bases. The PCR products can then be used for transient transfection.

The sequences of the invention can be a DNA, cDNA or other natural occurring, artificial or synthetic sequence derived from animals or humans, preferably mammals, more preferably humans. Also, the sequences of the invention comprise sequences complementary to SEQ ID NO: 1-109, transcripts thereof, or sequences that hybridize to any one of the disclosed sequences under stringent conditions.

Artificial sequences can be synthetic VREs (virus responsive elements) or ISREs (IFN-stimulated responsive elements). The synthetic or artificial sequences can also be a combination or repeat of VRE and ISRE sequences.

3. Cell Lines

The cell line may be any cell line known to the skilled person, preferably a Vero, 293T, K562, MDCK, HT1080, or HepGR, HT1080, or Huh-7 cell line, preferably a liver cell line, most preferably a Huh-7 cell line.

4. Array

The array of the invention comprises expression active response constructs as described above. A special embodiment disclosed herein is an array comprising reporter constructs with responsive elements that comprise at least three different sequences selected of SEQ ID NO: 4, SEQ ID NO:5, SEQ ID NO: 6, SEQ ID NO:7, SEQ ID NO: 8, SEQ ID NO: 9, SEQ ID NO:10 and SEQ ID NO: 11 (VREL1, VREL2, GIP3-6-16, MX1-1, MX1-2, USB18-M, IFIT3-2, PARP10). More preferably, the sequences are selected of SEQ ID NO: 12, SEQ ID NO:13, SEQ ID NO: 14, and SEQ ID NO: 58 (IFIT3-1, GBP1-V, VRE-Con, AB-VRE). These subsets of reporter constructs shows distinct differential reporter responses to NDV induction ranging from very weak to very strong (also see Example 4, Table 3, and FIG. 8). Such differential expression of the reporter gene allows specific determination of the trigger of IFN response and thus is an important tool for specific virus detection.

In a preferred embodiment, the array comprises reporter constructs with response elements that comprise at least two different sequences selected from SEQ ID NO: 4, SEQ ID NO:5, SEQ ID NO: 6, SEQ ID NO:7, SEQ ID NO: 8, SEQ ID NO: 9, SEQ ID NO:10, and SEQ ID NO: 11. More preferably, the sequences are selected from SEQ ID NO: 12, SEQ ID NO:13, SEQ ID NO: 14, and SEQ ID NO: 58.

In a preferred embodiment, the array comprises reporter constructs with response elements that comprise SEQ ID NO: 4 (VREL-1), SEQ ID NO: 11 (PARP10), SEQ ID NO: 16 (OAS3V2), and SEQ ID NO: 9 (USB18-M).

In yet another preferred embodiment, the array comprises reporter constructs with response elements that comprise SEQ ID NO: 16 (OAS3V2), SEQ ID NO: 10 (IFIT3-2), SEQ ID NO: 4 (VREL-1), SEQ ID NO: 53 (GIP3-6-16), SEQ ID NO: 5 (VREL-2), SEQ ID NO: 12 (IFIT3-1), SEQ ID NO: 78 (GPB1-V), SEQ ID NO: 14 (VRE Con), SEQ ID NO: 58 (AB VRE), SEQ ID NO: 62 (IFNA-V), SEQ ID NO: 33 (MX-1), SEQ ID NO: 15 (OAS3-V), and SEQ ID NO: 11 (PARP 10).

In yet another preferred embodiment, the array comprises reporter constructs with response elements that comprise SEQ ID NO:104 (AB-VRE-M2) SEQ ID NO: 5 (VREL-2), SEQ ID NO: 4 (VREL-1), SEQ ID NO: 100 (VRE-G1), SEQ ID NO: 9 (USB18-M), SEQ ID NO: 101 (SYN-ISRE-2R), SEQ ID NO: 19 (PARP10-S), SEQ ID NO: 11 (PARP10), SEQ ID NO: 16 (OAS3V2), SEQ ID NO: 15 (OAS3-V), SEQ ID NO:18 (MX1-2-2), SEQ ID NO: 33 (MX1), SEQ ID NO: 62 (IFNA-V), SEQ ID NO: 23 (IFIT3-2S), SEQ ID NO: 10 (IFIT3-2), SEQ ID NO: 12 (IFIT3-1), SEQ ID NO: 24 (IFIT1), SEQ ID NO: 78 (GPB1-V), SEQ ID NO: 53 (GIP3-6-16), SEQ ID NO:105 (AB-VRE-M), SEQ ID NO: 58 (AB-VRE), SEQ ID NO: 31 (HERC5), SEQ ID NO: 102 (SYN-ISRE-2), SEQ ID NO: 103 (B-VRE-3X), SEQ ID NO: 74 (PSMP9-V).

The advantage of such array is its specificity and versatility. As described below in the Examples, such array display a characteristic fluorescence pattern and can be used for the differentiation of IFN and Newcastle disease virus NDV (FIG. 6). Also, using the array for the method of the invention, viruses like Herpes simplex virus (HSV), EMC virus (EMCV), Vesicular stomatitis virus (VSV), influenza virus (FluV), and respiratory syncytial virus (RSV) may be detected and distinguished (FIG. 11). Other virus like hepatisic A, B, or C virus are may be detected as well.

An "array" or "microarray" refers to a multiplex technology used in molecular biology and in medicine. It consists of an arrayed series of several, many or even thousands of microscopic spots of molecules/probes (here: the constructs), called features. Typically, the molecules/probes are attached to a solid surface. The solid surface can be glass or a silicon or a plastic chip. Other microarray platforms use microscopic beads, instead of the large solid support. Arrays and microarrays are known in the art. In this application, the arrays and microarrays refer to any formats, including also 96-well plates, 384-well plates, and 1536-well plates, and higher content microarray, etc.

According to the invention, a preferred array platform/format uses vessels or vessel replicates, such as in microtiter plates.

Transfection and imaging of the reporter activity is performed according to methods known to the skilled person and as described in Example 1. The assessment and measurement of the reporter activity can be approaches, not only of the activity of the reporter proteins, but also of the levels of the reporter proteins. Reporter levels, whether intracellular or secreted, can be measured by any detection method including Western blotting, colorimetric method, fluorescence, luminescence, biosensors, and many others. Also, mRNA levels of the reporter can be used to monitor the transcription of the promoter. The mRNA levels can be assessed and quantified by a variety of techniques including, but not limited to, semi-quantitative PCR, real-time PCR, Northern blotting, RNase protection assay, beads-dependent mRNA quantification, in situ hybridization, and others.

Versatility of reporter systems allows use in many applications, for example, but not limited to, drug discovery, drug target discovery, bioassay development, bioassays, cytokine bioassays, interferon response bioassays, virus response bioassays, metal response bioassays, stress response bioassay, inflammatory response bioassays, cell growth assay, cellular behavior indicator assays, angiogenesis bioassay, chemotaxis and metastasis assays, hypoxia assays, environmental changes bioassays using parameters, such as heat, nutrient, radiation, oxygen, pH, salts, toxins. Additionally, any bioassay for inhibition of above responses is also a potential application.

The sensitivity of the molecular tools of the invention allow a more sensitive and differential method for detecting IFN and/or viral induction. Also, the sensitivity of the molecular tools of the invention as described above provide a reliable method for quantifying IFN potency and activity in pharmaceutical preparation or biological samples. The sensitivity of the reporter constructs of the invention also allow a reliable quantification method of virus activity.

Due to the specific expression pattern of the different reporter constructs of the invention as described above, and in particular due to the combination of certain reporter constructs, a method for distinguishing between IFN- and viral induction, and/or for distinguishing between different viruses can be provided. The combination of reporter constructs as described above is also necessary for a versatile and reliable method for the quantification of virus activity.

BRIEF DESCRIPTION OF THE DRAWINGS

FIG. 6 Differential expression of IFN and New Castle disease virus in human liver cells. Huh-7 cells (2×104) were seeded in 96-well microplates and transfected with 50 ng/well of the ISRE/VRE GFP reporter constructs for 16 hr. IFN (100 IU/ml) or NDV (10 HA per well) were added for 16 hr; fluorescence were quantitated from captured high resolution images using high-throughput BD bioimager and ProxCell algorithm (Hitti et al., 2010). Fold changes were evaluated by hierarchal clustering centered with Spearman's correlation. The designations of sequences—except synthetic variations-were derived from gene names in which the sequence elements were derived from.

FIG. 8 Monitoring of early (6 hr) and late response (16 hr) to IFN and virus challenge in the cell-based multiple reporter assay. Huh-7 cells (2×104) were seeded in 96-well microplates and transfected with 50 ng/well of the ISRE/VRE GFP reporter constructs for 16 hr. IFN (100 IU/ml) for early point (4-8 hr) or late point (16-20) hr; fluorescence were quantitated from captured high resolution images using high-throughput BD bioimager and ProxCell algorithm (Hitti et al., 2010). Fold changes were evaluated by hierarchal clustering centered with Spearman's correlation. The designations of sequences—except synthetic variations-were derived from gene names in which the sequence elements were derived from.

EXAMPLES

Example 1

Figure 1:
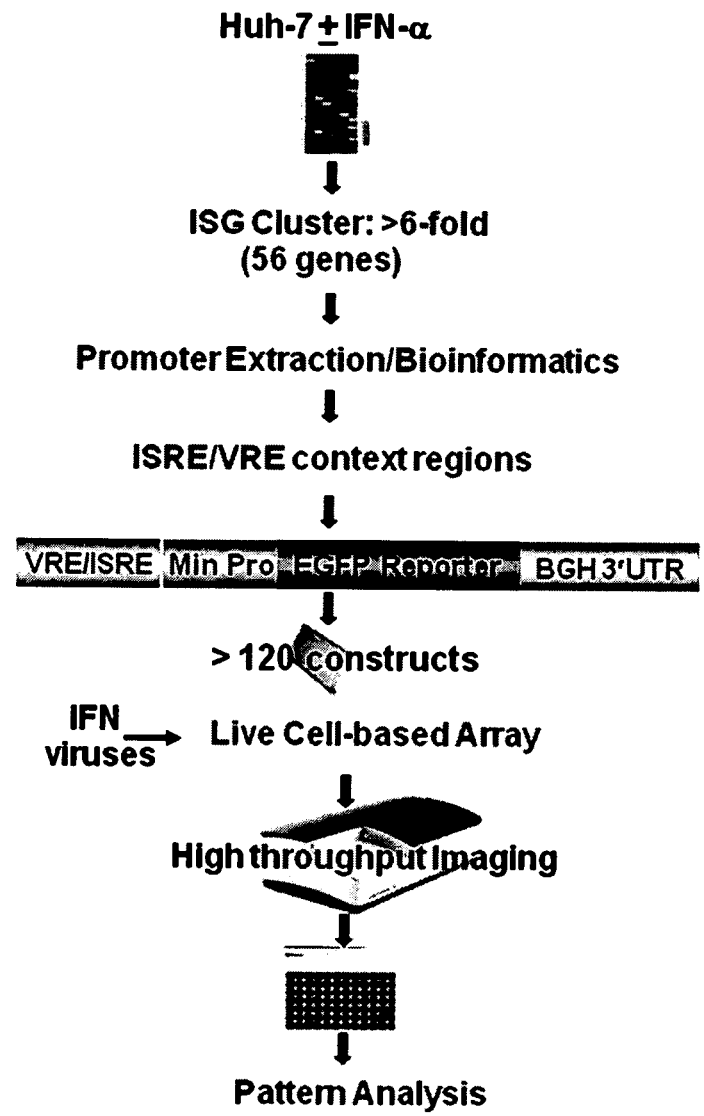
FIG. 1 Schematic representation of the GFP-based multiple IFN/Virus Reporter live cell System. The liver cell line, Huh-7, was treated with recombinant IFN-α (100 IU/ml) for 6 hrs. Total RNA extraction was performed and subjected to whole genome microarray hybridization and analysis. An IFN-stimulated gene (ISG) Cluster was analyzed using bioinformatics by extraction of the Promoter and searching for ISRE/VRE using Promoser (Halees et al., 2003) and TFSEARCH, respectively. Several variations of ISRE/VRE sequence elements with their context regions were utilized for construction of EGFP reporters. Cell-based 96-well arrays were assembled for use with various treatments of IFNs and viruses.

The following general methods were used in all subsequent Examples.
Cells, IFNs, and Viruses Huh-7 cells were maintained in DMEM medium supplemented with 10% heat-unactivated fetal bovine Serum (FBS), 100 U/ml penicillin, 100 pg/ml streptomycin. Recombinant human rIFNa2a (Roferon) is from Hoffman-LaRoche, Basel, Switzerland and had specific activity of 2×108 IU/mg. Recombinant human IFNy is from R & D systems. All viruses were obtained from ATCC and propagated in appropriate host cells. Encephalomyocarditis virus (EMCV), vesicular stomatitis virus (VSV, Indiana strain), Herpes simplex virus (HSV-I), respiratory syncytial virus, and influenza virus human H1N1 A/Puerto Rico/8/34 strain were obtained from the ATCC (Manassas, Va.). Virus preparations were clarified by low speed centrifugation, filtered through 0.22-pm membranes for sterility, and titrated on VERO (African Green Monkey Kidney cell line, ATCC) or by hemagglutinin assay (in case of RSV and flu virus). Virus stocks were aliquoted and stored at −70° C. until use.

Microarray Assessment of IFN-Stimulated Genes in the Human Transcriptome

Two whole genome expression analysis platforms were used, the OpArray whole transcriptome microarrays (Operon, Inc., USA) and whole transcriptome OneArray (Phalanx, Taiwan). The human liver cell line was treated with rIFN-α2a (100 IU/ml) for 6 hr incubation, which is optimal for the induction of many IFN-stimulated genes. Total RNA was extracted using Tri Reagent (Molecular Research Center, Cincinnati, Ohio). The microarrays were used for cohybridization, using Genisphere kit (Genisphere, Inc., Hatfield, Pa.); labeled cDNA generated from total RNA (20 pg) using Cy3 and Cy5 for control (medium only) and experiment (IFN treatment), respectively; details were previously described (Khabar et al., 2004). Scanning are performed with ScanArray Scanner (Perkin Elmer, Inc.) and the intensity of green and red fluorescent signals from each spotted cDNA sequence on the microarrays were calculated using adaptive circle algorithm and mean intensity of the pixels. Pre-processing, filtering of erroneous signals, normalization procedures, and calculation of intensity ratios were previously described in detail (Khabar et al., 2004)

Bioinformatics Analysis:

The IFN-stimulated gene list was utilized to extract their promoter sequences—in addition to—first intron and exon—using Promoser program. Promoser extract promoter regions based on transcriptional sites and alignment algorithms (Halees et al., 2003). Subsequently, a primary list of ISGs Promoters sequences were used to search for ISRE and VRE (e.g., IRF sites) using DNA Transcription Factor Binding Site Prediction TFSEARCH program context regions of—60 bases that harbor the ISRE/VRE sequences were extracted and the information were used for the forward primers' sequences.

Construction of IFN/Virus Response EGFP Reporters:

The method used to generate the reporter constructs utilizes the use of the destabilized EGFP plasmid previously described (al-Haj et al., 2009) and ISRE/VRE sequences containing primers. The expression active PCR products were generated directly from the EGFP vector using two primers. The forward primer contains 18 bases at the 3'end which targets a minimal promoter region of the CMV promoter upstream of the EGFP coding region, and the putative IFN/ISRE sequence context region. The reverse primer contains a complementary sequence to the downstream region of the poly (A) site. The oligonucleotides were custom-synthesized by Metabion (Germany). The PCRs were carried out using the following reagents and conditions: 2.5 U HotStart Taq (Qiagen) and 0.2 U Pfx polymerase (Invitrogen, Carlsbad, Calif.) mix, 2 pl (100-200 ng) of the vector template, 1× PCR buffer, 0.2 mM dNTP's, 0.2 pM primers, with the following cycle conditions: 95° C. for 12 min, 31 cycles of: 94"C, 1 min., 51° C., 1 min., 72° C., 4 min., and a final extension at 72° C. for 7 min. The PCR products were purified using Qiagen PCR purification columns to eliminate the primers, small PCR products, buffer, and enzymes. The PCR products were finally eluted in sterile water. The PCR products were run on a 1.2% agarose gel and visualized by ethidium bromide under UV light to verify size and quality. The purified PCR products were used in the transfection experiments.

Transient Transfection of ISG-Promoter Linked EGFP Reporter Constructs.

The promoter-reporter constructs were used in transient transfection at 50 ng per $2\times10^4$ cell/well in 96-well microplates. Transfection efficiency using cells in separate wells were evaluated using red fluorescent protein vector (TurboRFP, Invivogen). Transfections were performed in serum-free medium using LipofectAMINE 2000 (Invitrogen) for 6 h followed by replacing the medium with serum-supplemented medium. After 18 h incubation, IFNs or viruses were added for additional 18 h. Emission of green fluorescent levels are visualized by fluorescent microscopy.

Imaging and Fluorescence Measurement:

Efficiency and level of transfection were aided by monitoring the fluorescence from EGFP constnicts (optimum excitation wavelength: 488 nm and emission wavelength: 503 nm). Automated laser-fonis image capturing were performed using the high-throughput BD Pathway 435 imager (BD Biosciences, San Jose, Calif.). In all cases, exposure times and other Settings are kept constant to allow equal comparison of experiments. Automated identification and quantification are performed using Proxcell algorithms (Hitti et al., 2010). Data as fold increase over control are from mean values r standard error (SEM) of fluorescence intensiv. All transfections were performed in several replicates as indicated in the text. The variance in GFP fluorescence among replicate microwells was <6%; thus, with this minimum variance, experiments do not warrant transfection normalization. Image processing, segmentation, and fluorescence quantification was previously described (al-Haj et al., 2009). Student t-test was used when comparing two data groups while analysis of variance (ANOVA) was performed for each data Set having three or more data groups.

Quantitative Real-Time PCR

Isolated total RNA was reverse transcribed into cDNA using Superscript II (Invitrogen). The expression levels of EGFP mRNA and control housekeeping mRNA were assessed using TaqMan expression assay. First, reverse transcription was performed using Superscript II and Oligo dT primer (Invitrogen). A custom made Taqman primer and probe Set (Applied Biosystems) specific to EGFP reporter construct was used. The primers span the CMV promoter intron A in the EGFP vector to control DNA contamination. The 6-carboxyfluorescein (6FAM)-labeled TaqMan probe that target CMV exon 1-EGFP (exon 2) junction sequence was used. The probe design allowed further control of DNA contamination. The control GAPDH probe was labeled with a 5' reporter VIC dye (Applied Biosystems). The specificity for the cDNA of Taqman primer was tested on a negative control containing plasmid DNA. The endogenous control was used for normalization. Real time PCR was performed in multiplex in the Chroma 4 DNA Engine cycler (BioRad). The final results are expressed as normalized fold change in controls.

Example 2

VRE and ISRE-containing promoters that are responsive to IFN were searched by first profiling gene expression in the Huh7 liver cell line. 59 strongly induced (6 fold) gene cluster (FIG. 1, Table 1) have been selected.

TABLE 1

Table 1: Total RNA samples from mock-treated or IFN-α (100 U/ml)-treated cells were extracted and subjected to microarray-based hybridization. Microarray experiments were performed at least twice with two different whole transcriptome oligonucleotide microarray systems (as described in Example 1).

| Gene | Description | Induction, Ratio, Mean | SEM | N |
|---|---|---|---|---|
| ARF1 | ADP-ribosylation factor 1 | 5.20 | 0.20 | 2 |
| C10orf118 | Uncharacterized protein C10orf118 | 10.00 | 4.00 | 2 |
| C3 | complement component 3 | 5.58 | 1.93 | 2 |
| CASP7 | caspase 7, apoptosis-related cysteine peptidase | 6.11 | 0.80 | 2 |
| CXCL10 | chemokine (C-X-C motif) ligand 10 | 7.82 | 0.48 | 3 |
| DDX58 | DEAD (Asp-Glu-Ala-Asp) box polypeptide 58 | 13.00 | 4.28 | 2 |
| EPSTI1 | epithelial stromal interaction 1 (breast) | 19.00 | 2.00 | 2 |
| G1P2 | ISG15 ubiquitin-like modifier | 16.72 | 12.31 | 2 |
| G1P3 | interferon, alpha-inducible protein 6 | 16.00 | 2.00 | 3 |
| GBP1 | guanylate binding protein 1, interferon-inducible, 67 kDa | 12.65 | 3.62 | 4 |
| GBP3 | guanylate binding protein 3 | 5.92 | 0.86 | 3 |
| HERC5 | hect domain and RLD 5 | 18.02 | 2.56 | 2 |
| IFI27 | interferon, alpha-inducible protein 27 | 29.70 | 15.47 | 4 |
| IFI44 | interferon-induced protein 44 | 17.31 | 8.63 | 2 |
| IFIH1 | interferon induced with helicase C domain 1 | 8.24 | 0.07 | 2 |
| IFIT1 | interferon-induced protein with tetratricopeptide repeats 1 | 21.20 | 4.10 | 8 |
| IFIT2 | interferon-induced protein with tetratricopeptide repeats 2 | 18.72 | 6.44 | 3 |
| IFIT3 | interferon-induced protein with tetratricopeptide repeats 3 | 18.92 | 14.53 | 4 |
| IFIT5 | interferon-induced protein with tetratricopeptide repeats 5 | 5.61 | . | 1 |
| IFITM1 | interferon induced transmembrane protein 1 (9-27) | 16.58 | 6.62 | 2 |
| IRF1 | interferon regulatory factor 1 | 9.25 | . | 1 |
| ISG15 | ISG15 ubiquitin-like modifier | 9.02 | 6.77 | 2 |
| ISG20 | interferon stimulated exonuclease gene 20 kDa | 4.20 | 0.87 | 2 |
| ISGF3G | interferon regulatory factor 9 | 6.05 | . | 1 |
| LAP3 | leucine aminopeptidase 3 | 6.33 | 1.12 | 2 |
| MATR3 | small nucleolar RNA host gene 4 (non-protein coding) | 21.38 | 7.91 | 2 |
| MT2A | metallothionein 2A | 6.67 | 1.73 | 2 |
| MX1 | myxovirus (influenza virus) resistance 1 | 17.66 | 2.73 | 4 |
| MYD88 | myeloid differentiation primary response gene (88) | 5.01 | . | 1 |
| NPIP | nuclear pore complex interacting protein | 10.88 | 7.98 | 2 |
| NT5C3 | 5'-nucleotidase, cytosolic III | 6.66 | 0.78 | 4 |
| OAS1 | 2',5'-oligoadenylate synthetase 1, 40/46 kDa | 19.40 | 4.68 | 6 |
| OAS2 | 2'-5'-oligoadenylate synthetase 2, 69/71 kDa | 14.00 | 2.00 | 2 |
| OAS3 | 2'-5'-oligoadenylate synthetase 3, 100 kDa | 6.17 | . | 1 |
| OASL | 2'-5'-oligoadenylate synthetase-like | 7.72 | 0.00 | 2 |
| P4HB | prolyl 4-hydroxylase, beta polypeptide | 4.89 | 0.46 | 2 |
| PARP10 | poly (ADP-ribose) polymerase family, member 10 | 8.31 | 1.69 | 4 |
| PLSCR1 | phospholipid scramblase 1 | 9.41 | 0.58 | 2 |
| PPIA | peptidylprolyl isomerase A (cyclophilin A) | 20.34 | 1.35 | 2 |
| PRIC285 | Peroxisomal proliferator-activated receptor A-interacting complex 285 kDa | 5.82 | 0.11 | 2 |
| PSMB8 | proteasome (prosome, macropain) subunit, beta type, 8 | 10.17 | 1.40 | 2 |
| PSMB9 | proteasome (prosome, macropain) subunit, beta type, 9 | 11.95 | 0.81 | 3 |
| PSMD1 | proteasome (prosome, macropain) 26S subunit, non-ATPase | 8.45 | | 1 |
| PSME1 | proteasome (prosome, macropain) activator subunit 1 | 3.64 | | 1 |
| SAMD9 | sterile alpha motif domain containing 9 | 7.18 | 2.97 | 2 |
| SELPLG | selectin P ligand | 64.43 | | 1 |
| SLC15A3 | solute carrier family 15, member 3 | 6.00 | 0.04 | 2 |
| SP100 | SP100 nuclear antigen | 8.00 | 2.00 | 2 |
| STAT1 | signal transducer and activator of transcription 1, 91 kDa | 11.37 | 4.19 | 4 |
| STAT2 | signal transducer and activator of transcription 2, 113 kDa | 9.35 | 5.76 | 2 |
| TAP1 | transporter 1, ATP-binding cassette, sub-family B (MDR/TAP) | 13.98 | 2.90 | 4 |
| TMEM67 | transmembrane protein 67 | 22.00 | | 1 |
| TRIM22 | tripartite motif-containing 22 | 19.00 | 2.00 | 2 |
| UBE2L6 | ubiquitin-conjugating enzyme E2L 6 | 9.98 | 5.86 | 3 |
| USP18 | ubiquitin specific peptidase 18 | 14.33 | 3.50 | 5 |
| TMEM67 | transmembrane protein 67 | 22.00 | | 1 |
| TRIM22 | tripartite motif-containing 22 | 19.00 | 2.00 | 2 |
| UBE2L6 | ubiquitin-conjugating enzyme E2L 6 | 9.98 | 5.86 | 3 |
| USP18 | ubiquitin specific peptidase 18 | 14.33 | 3.50 | 5 |

Data are Mean ± SEM of normalized ratios. N: number of replicate spots.

Their promoters have been bioinformatically extracted and regions that contain VRE and ISREs (FIG. 1) have been searched.

From each promoter, sequences matching the consensus elements of IRF-1, IRF-2, STATx, and ISRE (80% match) were extracted with their flanking region of 40-70 nucleotides; then, ~100 VRE/ISRE regions were compiled (Table 2).

TABLE 2

Sequence Information for ISRE/VRE regions

| SEQ ID NO: | Gene cluster | Sequence |
| --- | --- | --- |
| SEQ ID NO: 4 | VREL1 | GGGAAACCGAAACTGGGGAAACCGAAACTGGGGAAACCGAAAC<br>TGGGAAACCGAAAC |
| SEQ ID NO: 5 | VREL2 | GGAAACCGAAAGGGGAAAGTGAAACTAAAGCTGAAACCGAAAG<br>GGGAAAGTGAAACTAAAGC |
| SEQ ID NO: 6 | GP3-6-16 | GGGAAAATGAAACTCGGAGCTGGGAGAGAGGGGAAAATGAAAC<br>TGCAGAAATAGAA |
| SEQ ID NO: 7 | MX1-1 | GCTAGGTTTCGTTTCTGCGCCCACAGGGTCTGTGAGTTTCATTTC<br>TTC |
| SEQ ID NO: 8 | MX1-2 | TGAGTTTCGTTTCTGAGCTCCTTTCATTTTCACCGGTTTCAAT-<br>TCTC<br>CTCTGGA |
| SEQ ID NO: 9 | USB18-M | CTCCCGGCGCGGAGGCCGCTGTAAGTTTCGCTTTCCATTCAGTGG<br>AAAACGAAA |
| SEQ ID NO: 10 | IFIT3-2 | GATTCTGTTTCAGTTTCCCCTCAAGAGGGATCTTGATAGGGTTCCA<br>TCAGTTTCACTTTCCTTTCCCCTTTCATCC |
| SEQ ID NO: 11 | PARP10 | CCTCCTTCCG TCTTTCAGTT<br>TCACTTTTGTTTTCCTGCTCCTGCTCCCTC |
| SEQ ID NO: 12 | IFIT3-1 | GTTTCATTTTCCTCCTCCCAACGATTTTAAATT-<br>AGTTTCACTTTCCA<br>GTTTCCTCTTCCTT |
| SEQ ID NO: 13 | GBP1-V | AAAAAACTGAAACTCAGCCTGAAAGATGAACAGAACAAAACAG<br>AAATCCT |
| SEQ ID NO: 14 | VRE Con | GAAAGTGAAAAGAGAAATGGAAAGTGGAAAAGGAGAAACT |
| SEQ ID NO: 15 | OAS3-V | AGTGTCTGATTTGCAAAAGG AAAGTGCAAAGACAGCTCCT<br>CCCTTCTGAGG |
| SEQ ID NO: 16 | OAS3-V2 | TTCGGAGAGCCGGGCGGGAAAACGAAACCAGAAATCCGAAGGC<br>CGCGCCAG |
| SEQ ID NO: 17 | MX1-1-2 | GCTAGGTTTCGTTTCTGCGCCCACAGGGTCTGTGAGTTTCATTTC<br>TTCGCG |
| SEQ ID NO: 18 | MX1-2-2 | TGAGTTTCGTTTCTGAGCTCCTTTCATTTTCACCGGTTTCAAT-<br>TCTC<br>CTCTGGAG |
| SEQ ID NO: 19 | PARP10S | CTCCTTCCGTCTTTCAGTTTCACTTTTGTTTTCCTGCTCA-<br>GTTTCAC<br>TTTTGTTTT |
| SEQ ID NO: 20 | DZIP1 | CAGCTTCAGTTTTCCTAATGACAGTGAGTCATTTCT-<br>TCTCTCTCTTT<br>T |
| SEQ ID NO: 21 | DZIP1-2 | CCATTTCCCTCCCTCCTCTCATAGACAACCGA-<br>TATATATCTTTCACT<br>TTGGTG |
| SEQ ID NO: 22 | IFIT3-1-1 | GTTTCATTTTCCTCCTCCCAACGATTTTAAATT-<br>AGTTTCACTTTCCA<br>GTTTCCTCTTCCTT |
| SEQ ID NO: 23 | IFIT3-2S | G ATTCTGTTTCAGTTTCCCCTCAGTTTCACTTTCCTTTC-<br>CCCTTTC<br>AGCAGTTTCACTTTCCTTTCCCCTTT |

TABLE 2-continued

Sequence Information for ISRE/VRE regions

| SEQ ID NO: | Gene cluster | Sequence |
|---|---|---|
| SEQ ID NO: 24 | IFIT1 | TCCGCTAGCTTTAGTTTCACTTTCCCCTTTCGGTTTCCCTAG-GTTTCCAACTTG |
| SEQ ID NO: 25 | IFIT2 | AGTCCTGCCAATTTCACTTTCTAGTTTCACTTTCCCTTTTG-TAACGTCAGCTG |
| SEQ ID NO: 26 | TMEM67 | CCTTCTCTTTCCCTTTCCAGCACTTTGATTCCTTGTGGTGTCT-GTTTCTGTTTTGTTAGTAATTTCATG |
| SEQ ID NO: 27 | MATR3-1 | ATCTCCATCAAACCAAGATCCTAAGGGCTGGAAGTTTGTCTTTTCCATCATTG |
| SEQ ID NO: 28 | MATR3-2 | AAAGTTTGACTTTCTCTGCACAGTTCCACTTTCAGAGTTTTGCTTTTGTTG |
| SEQ ID NO: 29 | MATR3-3 | TCTCATTTTCATTTTTACCTGTTTTGTCTTACTTTGTACTTTAC-CCAGTTTCGCTTTATCATCTG |
| SEQ ID NO: 30 | OAS1 | GATGATCTTTCCACTTCCTGGTTTTTCTGACTTTTTTTCTTTTTGCAGTG |
| SEQ ID NO: 31 | HERC5 | GTTTCCTTTTCCTTTTCGATTCCGCCCCCTAACATTAT-GTTTCGTTTTCCACTG |
| SEQ ID NO: 32 | USP18 | CCAGCTCCCGGCGCGGAGGCCGCTGTAAGTTTCGCTTTCCATTCAGTGGAG |
| SEQ ID NO: 33 | MX1 | GCTAGGTTTCGTTTCTGCGCCCCACAGGGTCTGTGAGTTTCATTTCTTCGCG |
| SEQ ID NO: 34 | MX1-2-3 | TGAGTTTCGTTTCTGAGCTCCTTTCATTTTCACCGGTTTCAAT-TCTCCTCTGGAG |
| SEQ ID NO: 35 | IFI44 | GGGCTGGGCACACTGAGTTTCAGTTTCCTTTCTCTGAGTCTTTGAAGCTTCG |
| SEQ ID NO: 36 | IFI44-2 | GGTAAATGTCTTTCTGCTTTTCATTTTTCCTAGCTAGCATTAGTCTCTCTG |
| SEQ ID NO: 37 | DDX58 | CCGCTAGTTG CACTTTCGATTTTCCCTTTAGTTATTAAAGTTCCTATGCAG |
| SEQ ID NO: 38 | ISG15 | AGTCCCCGCCACTTTTGCTTTTCCCTGTCTTTCGGTCATTCGGTTTTGTTTCTTCCG |
| SEQ ID NO: 39 | STAT1 | GCTGCCTTTTCTCCTGCCGGGTAGTTTCGCTTTCCTGCGCAGAGTCTGCGGAG |
| SEQ ID NO: 40 | IPARP10-1 | CCTCCTTCCGTCTTTCAGTTTCACTTTTGTTTTCCTGCTCCT-GCTCCCTCG |
| SEQ ID NO: 41 | IFIH1 | AATTCGCTTTCCTTTTCTGTTTCCCGCGGTGTCCTTAACCAAAGGCCTCCTCTCTTCA |
| SEQ ID NO: 42 | CASP7-1 | TGATATCTTATTGIGGTTFTGCTTTGCATTTCCCTGTGAGCAC-CTTTTCATATG |
| SEQ ID NO: 43 | CASP7-2 | CACTTCTTTCAAAGTGGTTTCTTTCAGTTTTCCTATTAAGTTC-CTGTGTTGCTTCTTG |
| SEQ ID NO: 44 | CASP7-3 | AGTTTTCTGTCTAATTTCTTTTCTACCCTTTTCTCTTTGCTCCT-TCTGAGACA |
| SEQ ID NO: 45 | CASP7-4 | CCATTCTTTTATTCCTTTACCTTTGCTTTCACTTTACTCTACCCT-TAATTCTTTCTTG |

TABLE 2-continued

Sequence Information for ISRE/VRE regions

| SEQ ID NO: | Gene cluster | Sequence |
|---|---|---|
| SEQ ID NO: 46 | NT5C3-1 | ACTCTTTGCTATTTAGTTTCATTTTTGTTTTAAGTTTCACTTT-GCAG CTGTTTCTTTTT |
| SEQ ID NO: 47 | NT5C3-2 | AGGTTCCTCTTTTCTTTCCAGAGCCAGTTGACAGATTTACCTTCTC TTTAAG |
| SEQ ID NO: 48 | NT5C3-3 | ACAGTTTTAGCTTTACAATTTTTTTTCTCTTTCCTTTTGTTGT-GAAT TCATTTACCTAACG |
| SEQ ID NO: 49 | SAMD9 | ATTTGACTTCCTCTTTTCCTAACTGAATACTCTTTATTTCTT-TATCCT GCCTAAGAACTT |
| SEQ ID NO: 50 | C13ORF18 | CAATTTCACTTTTATTCCTCTTTCTTCTCCTTACCTATTTTT-GACACA TTTATTCAGTATG |
| SEQ ID NO: 51 | PSMP8 | CTGTGGCTTTCGCTTTCACTTCCTCCTCTTTCGCTTTCACTTC-CTCC CCGAGA G |
| SEQ ID NO: 52 | ISRE-74 | AGCTTTAGTTTCACTTTCCCCTTTCGGTTTCAGCTT-TAGTTTCACTT TCCCCTTTCGGTTTCCG |
| SEQ ID NO: 53 | GIP3-6-16 | GGGAAAATGAAACTCGGAGCTGGGAGAGAGGGGAAAATGAAAC TGCAGAAATAGAAACTG |
| SEQ ID NO: 54 | IFNA4 | AAGTAAAGAAAGTGAAAGTGAAAAGGAGATTGGAAAGCAAGGA AAGGAGAAACG |
| SEQ ID NO: 55 | 7XVRE1 | GAAAGTGAAAGTGAAAGTGAAAGTGAAAGTGAAAGTGAAAGTG |
| SEQ ID NO: 56 | PRD2X | GAAAGTGAAAAGAGAATTGGAAAGCGAAAGTGAAAAGAGAATT GGAAAGCG |
| SEQ ID NO: 57 | 7VRE2 | AAGTGAAAGTGAAAGTGAAAGTGAAAGTGAAAGTGAA AGTG |
| SEQ ID NO: 58 | AB-VRE | AGAAATGGAAAGTAGAAATGGAAAGTGAGAAGTGAAAGTGAGA AGTGAAAGTG |
| SEQ ID NO: 59 | VREL-3 | GGGAAAGAGAAACCGGAAAAGCGAAACTGGAAAGAGAAACCGG AAAAGCGAAACTG |
| SEQ ID NO: 60 | ISG15-M | ACTTTTGCTTTTCCCTGTCTTTCGGTCATTCGGTTTTGTTTCT-TCCG GGAAAGGGAAACCGAAACTGAAG |
| SEQ ID NO: 61 | IFIT2-M | AAGAAAAAGAGTCCTGCCAATTTCACTTTCTAGTTTCACTTTCCCT TTTGTTGAAGGGAAACAAACAAAAAGGAA |
| SEQ ID NO: 62 | IFNA-V | GAGAAACATAAAGAGTGCATGAAGGAAAGCAAAAACAGAAATG GAAAGTGGCCCATTAAGAAAGTGGAAATCAG |
| SEQ ID NO: 63 | IFNO-V | CACAAATGAAAACAGTAAAAGAAACTGAA AGTACAGAGAAATGTTCAGAAAATGAAAACCATGTGT |
| SEQ ID NO: 64 | IFNA5 | TAGAAAGAGCATAAAAGAAAGCAAAAAGAGAAGTAGAAAGTAG GCAAGAAAATGGAAACTGTGACCTTG |
| SEQ ID NO: 65 | RGS20-V | CAGCAAAGTGGAACTTAAGAGGGGAAGTGAAACAGGGAAATGC AAGGAGAAAGGCGAAAG |
| SEQ ID NO: 66 | C13ORF18-V | CTGAAAGATGACTCAGTTAAGAAGCTGGAAAATAAAACCAGGTC TTATTCTGAACTGAAAGTC |
| SEQ ID NO: 67 | SELPLG-M | AGATGGGCACTGTTTCTTATCCCAATTTTACAGATGGGAAACTGA AGCTCAGGGAGGCAAG |
| SEQ ID NO: 68 | PKR-V | AGTAGAAAAGAGCAAGTCTAAGGAATATCTAGAAAAGAGGAAGT TAGAACCATAGAAAAGG |

TABLE 2-continued

Sequence Information for ISRE/VRE regions

| SEQ ID NO: | Gene cluster | Sequence |
|---|---|---|
| SEQ ID NO: 69 | PKR-I | TGAATTATTTCTCCTCCTTCAATTTCAGTTTGCTCATACTTTGTGAC TTGCGGTCACAGTG |
| SEQ ID NO: 70 | IF127-1 | ATGAGGGGAGAAAGATGTCTGCAGTTTCGGTTTCCTGGAAAATGA AACCTGG |
| SEQ ID NO: 71 | IF27-2V | AGTGTCTGATTTGCAAAAGGAAAGTGCAAAGACAGCTCCTCCCTT CTGAGG |
| SEQ ID NO: 72 | TMEM67-V | TGTAAATGGAAAAACGAAATGACAAATAATTATGAAAGAGGCATC CATTTG |
| SEQ ID NO: 73 | TAPI | TGAGCAGGCGGCCGCTTTCGATTTCGCTTTCCCCTAAATGGCTGA GCTTG |
| SEQ ID NO: 74 | PSMP9-V | CAGCCATTTAGGGGAAAGCGAAATCGAAAGCGGCCGCCTGG |
| SEQ ID NO: 75 | IFITM1-V | ACAGCAGGAAATAGAAACTTAAGAGAAATACACACTTCTGAGAA ACTGAAACGACG |
| SEQ ID NO: 76 | ISG15-V | TGCCTCGGGAAAGGGAAACCGAAACTGAAGCCAAATTTGGCCAG |
| SEQ ID NO: 77 | IFIT2-V | TGTAACGTCAGCTGAAGGGAAACAAACAAAAAGGAACCAGAGG CCACG |
| SEQ ID NO: 78 | GPB1-V | AAAAAACTGAAACTCAGCCTGAAAGATGAACAGAACAAAACAG AAATCCTG |
| SEQ ID NO: 79 | GPB3-AV | ACACGGTTATAGACAAAGAAAAAACTGAAACCCAGCATCAAAGA GGAACAG |
| SEQ ID NO: 80 | GPB3-BV | TACAAAATGGAAAAACAGAACAAAACAGAAAACCTAAAGCTGTA TTGCTGG |
| SEQ ID NO: 81 | C10ORF18 | AGTAGTAAGTTTTGCTTTACAAATTCTTACATTGCAGAATCGTCTG CATCAGCTAG |
| SEQ ID NO: 82 | PLSCR1V | CGCCAGCGCGGGAACCGGGAAAAGGAAACCGTGTTGTGTACGTA AGATTCG |
| SEQ ID NO: 83 | OAS3V-2 | GCTGCTAGAAAGAAACGAAACTGAAAGCAGGGAATG |
| SEQ ID NO: 84 | EPSTI1 | CTTTGTAGGTTTTTGTTTTCTTTTGATTTCAGTTTCCATTTCCTCTG |
| SEQ ID NO: 85 | SP100 | GTTAAATACTTTCACTTCTCTTTTCCCCATTTGGGCGGAGCCCTTT CTGAGTCAGTCG |
| SEQ ID NO: 86 | NFKBI | TGCAGGGAAGTACCGGGAAGGACTTTCCAGCGCAGGGAGTTTCT CCGCTTGGAAATTCCCCGG |
| SEQ ID NO: 87 | IRF-7-V | GTAACAAAAGCGAAACTCCATCTCAAAAAAAGAAACGCAAGG |
| SEQ ID NO: 88 | IFNB | AAATGTAAATGACATAGGAAAACTGAAAGGGAGAAGTGAAAGTG GGAAATTCCTCTGAATG |
| SEQ ID NO: 89 | IFNB-2 | CTAAAATGTAAATGACATAGGAAAACTGAAAGGGAGAAGTGAAA G TGGGAAATTCCTCT |
| SEQ ID NO: 90 | USB18-V | TGCTATTATGAAGGAAAAAGTGAAATGGAAATTAAAAAC |
| SEQ ID NO: 91 | GAS | CTCGGGAAAGGGAAACCGAAACTGAAGCC |
| SEQ ID NO: 92 | GAS-2 | AGCCTGATTTCCCCGAAATGACGGCAGCCTGATTTCCCCGAAATG ACG |
| SEQ ID NO: 93 | CXCL-10A | TTTCAGAAACAGTTCATGTTTTGGAAAGTGAAACCTAATTCACTAT TACCAAAAAAGAGGAGCAGAGG |
| SEQ ID NO: 94 | CXCL-10B | TGATGTTTTCATTCAGGGACTTGAAACTTGTTTTAACACATGAGCA ATGTTTTCCCTCAAAATAG |
| SEQ ID NO: 95 | IRF-9 | AAGGCCCTCCCTGGAGGAGAACTGAAACTTAGGGTGGGGACTGT AGAAAG |

TABLE 2-continued

Sequence Information for ISRE/VRE regions

| SEQ ID NO: | Gene cluster | Sequence |
|---|---|---|
| SEQ ID NO: 96 | myd88 | AGGGCGGCGCAGGGCGGCGCTTCTCGGAAAGCGAAAGCCGGCG GGGCG |
| SEQ ID NO: 97 | IRF-3 | CTTCTGAGTCTTAGAGAAAAAGGAACTGGAGCCCCAGACC |
| SEQ ID NO: 98 | IFNA17 | AACACATGTAGAGAGTGCAAAAAGAAAGCAAAAACAGACATAGA AAGTAA |
| SEQ ID NO: 99 | IFNA1-V2 | GAGTGCATGAAGGAAAGCAAAAACAGAAATGGAAAGTGGCCCA GAA |
| SEQ ID NO: 100 | VRE GI | GGGAAACCGAAAGTGGGAAACCGAAAGTGGGAAACCGAAAGTG GGAAACCGAAAGTG |
| SEQ ID NO: 101 | SynISRE-2R | TACTTTCGCTTTCCACTTTCGCTTTCCTCACTTTCGCTTTC- CTACTT TCGCTTT |
| SEQ ID NO: 102 | synISRE-2 | GGGAAACCGAAACTAGGAAACCGAAACTGAGGAAACCGAAACT GGAAACCGAAACTA |
| SEQ ID NO: 103 | B-VRE-3X | GAGAAGTGAAAGTGAGAAGTGAAAGTGAGAAGTGAAAGTG |
| SEQ ID NO:: 104 | AB-VRE-M2 | AGAAATGGAAAGTGAGAAGTGAAAGTAGAAATGGAAAGTGAGA AGTGAAAGTG |
| SEQ ID NO:: 105 | AB-VRE-M | AGAAATGGAAAGTAGAAATGGAAAGTACTGCGAGAAGTGAAAGT GAGAAGTGAAAGT |
| SEQ ID NO: 106 | OAS1-V | AGTGTCTGATTTGCAAAAGGAAAGTGCAAAGACAGCTCCTCCCTT CTGAGG |
| SEQ ID NO: 107 | OAS3-V2-2 | GCTGCTAGAAAGAAACGAAACTGAAAGCAGGGAATG |
| SEQ ID NO: 108 | SYNVRE-1 | GGGAAACCGAAAGTAGGAAACCGAAAGTGAGGAAACCGAAAGT GGAAACCGAAAGTA |
| SEQ ID NO: 109 | VRE-G2 | GGGAAAGCGAAAGTGGGAAAGCGAAAGTGGGAAAGCGAAAGTG GGAAAGCGAAAGTG |

The VRE and ISRE sequences are found in IFN genes and IFN-stimulated genes, and partially overlap each other, particularly the core sequence AANNGAAA with the following consensus sequences GAAANNGAAASY (SEQ ID NO:1), wherein S is G, or C, and Y is T, or C, and N is A, C, G, or T/U; or GAAAANNGAAASY (SEQ ID NO:2), wherein S is Q or C, and Y is T, or C. and N is A, C, Q or T/U, or RNGAAANNGAAACT (SEQ ID NO:3), wherein N is A, C, G, or T/U (also in complementary strand), respectively (Savitsky et al., 2010; Pierre et al., 2009).

Example 3

Figure 2:
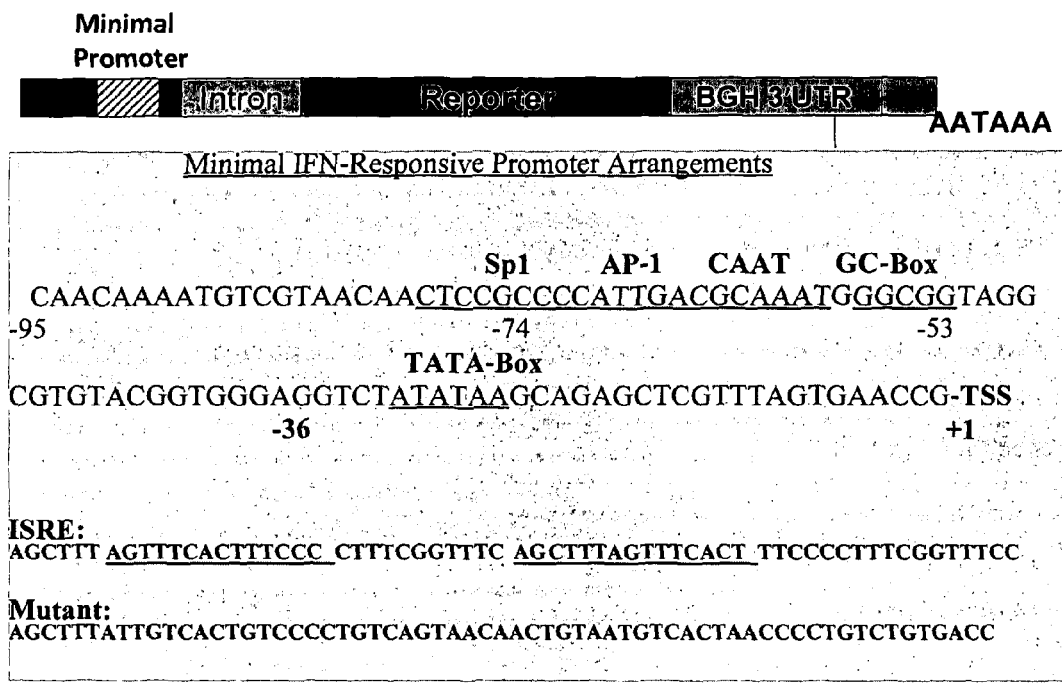
FIG. 2 Graphical scheme showing the minimal promoter of CMV IE promoter used for the IFN-responsive construct. TSS: transcriptional start site (SEQ ID NO:110); mutant (SEQ ID NO:111); ISRE (nucleotides 1-63 of SEQ ID NO:52). Numbers are in relation to TSS.

In order to proceed with constructing the virus/IFN responsive constructs the VRE/ISRE response GFP reporter were optimized by assessing several IFN-responsive reporter constructs using a consensus ISRE with different minimal promoters (-36, -53, and -74 from the transcriptional start site following IE CMV promoter) (FIG. 2). The optimal -74 CMV reporter response required the following cis-acting elements: TATA box, GC-Box, CAAT signal, and AP-1 site. Further minimal promoter (-53) contained only the TATA box but it is necessary to extend the length beyond the TATA box with additional 24 nucleotides since -36 region minimal promoter which contains only the TATA box failed to induce IFN response.

Figure 3:
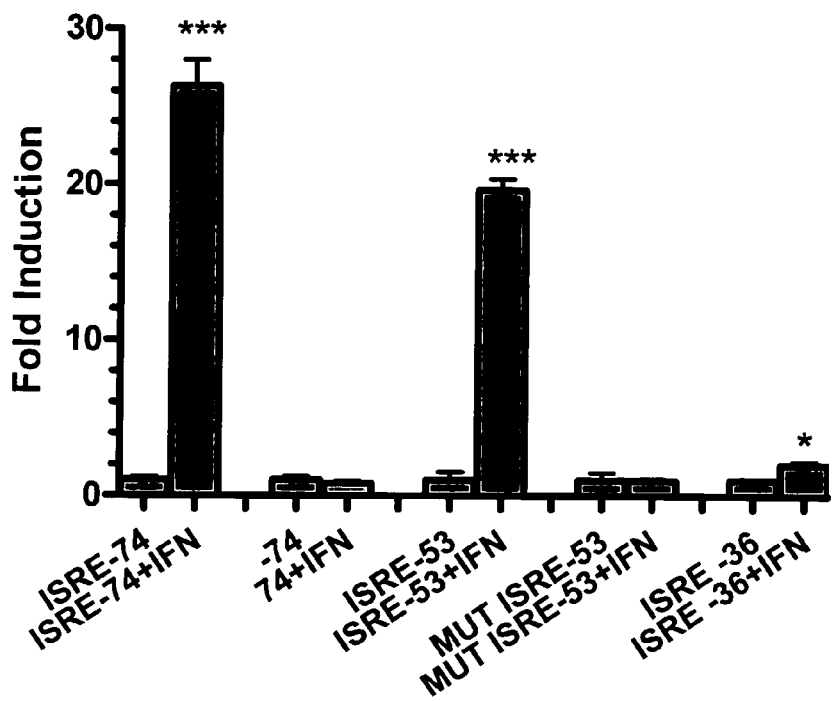
FIG. 3 Reporter activity of EGFP reporter constructs. EGFP reporter constructs were used for transient transfection of Huh-7 cells for overnight. IFN-α (100 U/ml) were added for 16 hr. Fluorescence was quantified as described in Methods. Reporter activity as fluorescence was assessed from images captured by BD automated bioimager and quantitated by ProXcell (as described in Example 1). Readings are Mean±SEM of fold increase over control from fluorescence intensities of quadruplicate wells. ***$p<0.001$ AND *$<0.01$ using Student's t-test.

In this example, Huh-7 cells were transfected with the reporter using -74 or -53 minimal promoter fused with standard IFN-responsive elements (as shown in FIG. 2). Additionally, mutant -53 promoter was used (sequence showing in FIG. 2). There was indeed significant responses with -74 and -53 constructs but not with -36 constructs. -74 constructs gave higher induction in contrasts to -53 constructs (FIG. 3).

Figure 4:
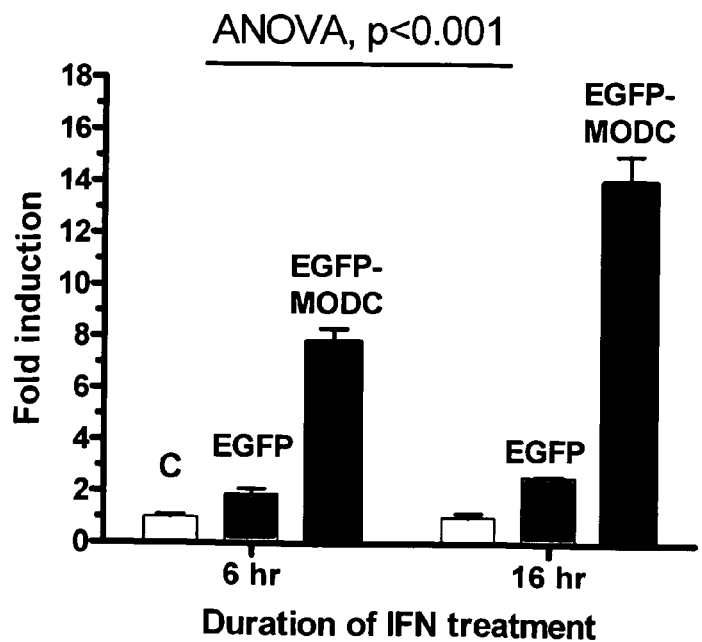
FIG. 4 Early response performance comparison between EGFP and EGFP-MODC (destabilized EGFP). Reporter Expression constructs containing either wild type EGFP or unstable EGFP-MODC fusion protein were transfected onto Huh-7 cells. Cells were cultured in the presence or absence of 100 U/ml of IFN-α for the indicated period of time. Fluorescence levels were measured (as described in Example 1). High resolution images were obtained automatically by BD high-content imager. Quantitation was performed with Proxcell imaging algorithm. Data is fold difference in Mean±SEM (quadruplicate) from a representative experiment of two.
Figure 5:
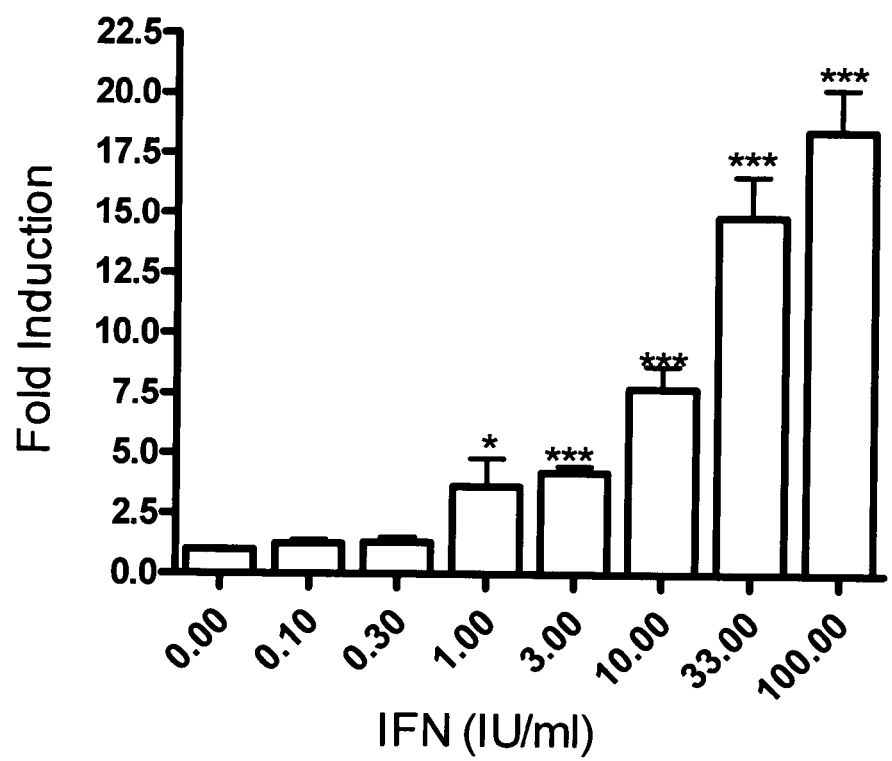
FIG. 5 Dose-response characteristics of ISRE-containing EGFP-MODC reporter. The ISRE-containing destabilized EGFP reporter construct was used for transient transfection of Huh-7 cells. Increasing doses of IFN were added to the cells for 16 hr. Fluorescence was quantified (as described in Example 1). Reporter activity as fluorescence was assessed from images captured by BD automated bioimager and quantitated by ProXcell as described in Methods. Readings are Mean±SEM of fold increase over control from fluorescence intensities of quadruplicate wells. ***$p<0.001$ AND *$<0.01$ using Student's t-test.

The use of the MODC C-terminus amino acids to destabilize the GFP protein contributed to better and earlier response (e.g., four to eight hours, FIG. 4) to IFN since MODC contains the protein instability determinants, PEST, known to occur in many proteins with short half life (Li et al., 1998). The benefit of earlier response is to allow flexibility in assay development and alternative drug screening approaches. Overall, the reporter construct had excellent linear dynamics response (1 IU/ml-100 IU/ml) sensitivity, and rapid kinetics—FIG. 5).

Example 4

Approximately 100 IFN/virus responsive GFP constructs (FIG. 1) were created. Sequence information was obtained from the bioinformatics (Table 2). The ISRE/VRE appears to be heterogeneous in terms of the sequence element reiterations and deviations from their Consensus, the number of ISRE repeats and their distribution in the entire promoter. Thus, the GFP reporter array was created so that differential fluorescence patterns from reporters with different sequence element heterogeneity due to IFN and virus can be monitored. The GFP 96-well microplate arrays contain lyophilized DNA for use in a number of transfection array experiments.

The Huh-7 cells were transfected with the VRE/ISRE GFP constructs and then treated with medium, IFN or virus for 6 and 16 hr duration, representing early and late response; respectively. IFN was able to induce a significant subset of both ISRE and VRE containing constructs at 16 hr. In many instances, the VRE/ISRE act as common signature for both IFN and virus response but there are distinct patterns between IFN and the New Castle disease virus (NDV) responses (FIG. 6). Using hierarchal clustering normalized to Spearman's rank correlation, distinct patterns were observed that distinguishes IFN and NDV.

Figure 7:
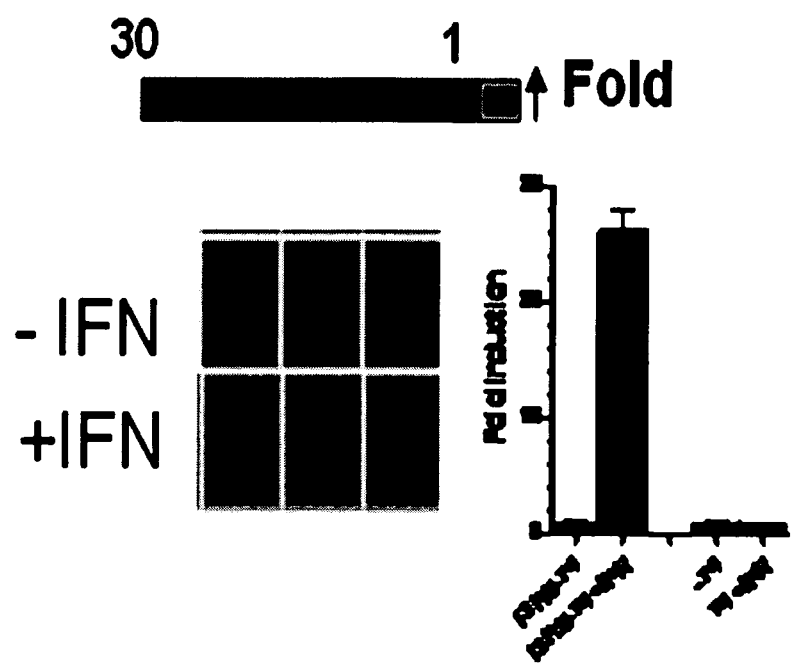
FIG. 7 An image of live cells showing the induction by IFN (left) and mathematical/statistical graph of the result (right). A reporter with mutant response elements is as control.
Figure 8:
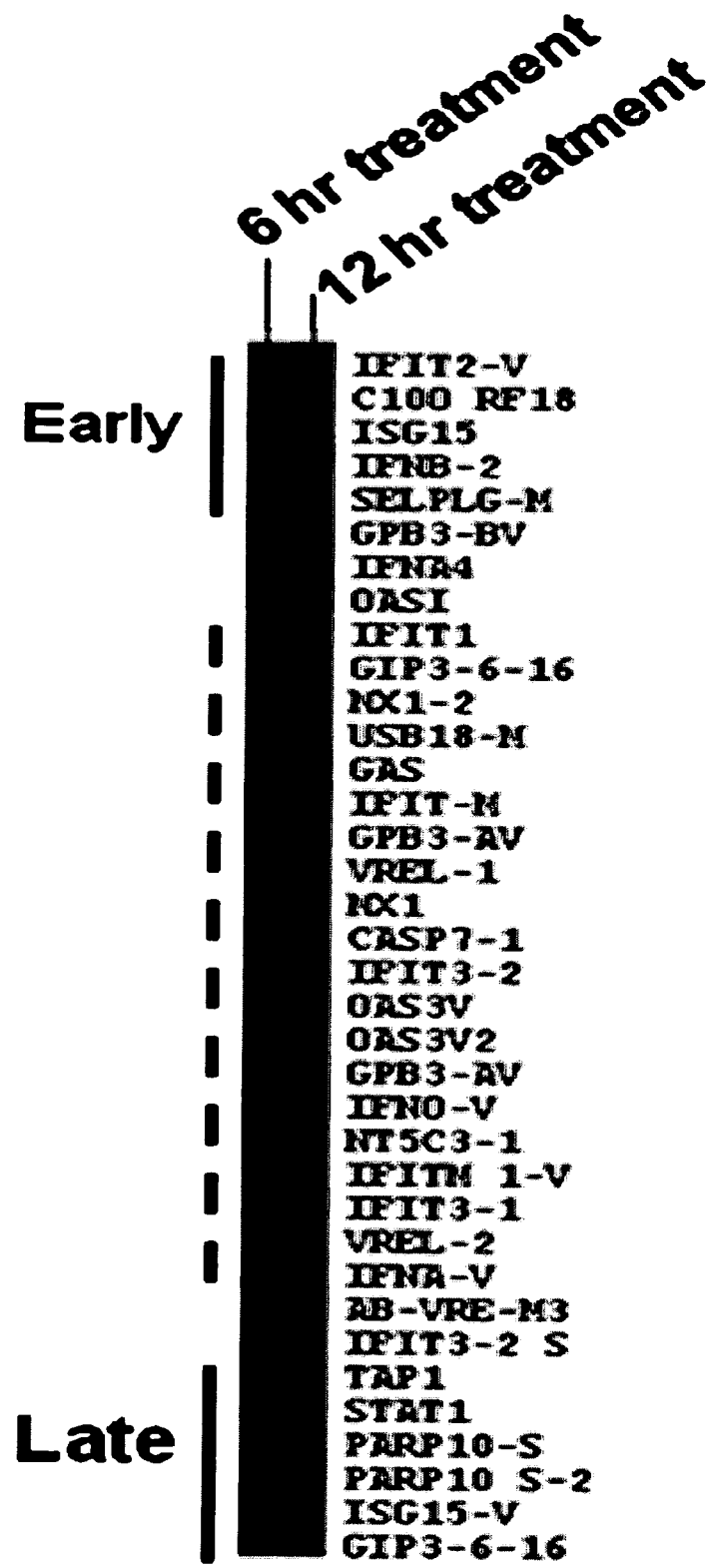

There was a subset of GFP reporters that respond more strongly to virus than IFN and vice versa (FIG. 6, right and left column, respectively). FIG. 7 shows an image and graph example of the performance of the reporter. Within IFN responsive subset, there were distinct differential reporter responses ranging from very weak effect to stronger effects (1.5-33-fold). The strongest IFN-specific effect was observed with two synthetic sequences (designated, as VREL-1 (SEQ ID NO: 4) and VREL2 (SEQ ID NO: 5) that comprise four copies of GGGAAACCGAAACTG (nucleotides 1-15 and 31-45 of SEQ ID NO:4) or GAAACTAAAGCTG (nucleotides 21-33 of SEQ ID NO:5) repeats (30-33 fold increase). The naturally derived sequences GIP3-6-16 (SEQ ID NO: 53), MX1-1(SEQ ID NO: 33), MX1-2(SEQ ID NO: 8), USB 18-M (SEQ ID NO: 9), IFIT3-2 (SEQ ID NO: 10), and PARP10 (SEQ ID NO: 11) caused strong induction by IFN (.about.2.0 fold, p<0.0001) but with variable levels of induction by the virus (FIG. 8, Table 3).

TABLE 3

Table 3: Huh-7 cells were transfected with different constructs and then treated with IFN for brief (4-8) or longer duration (24 hr). Subsequently, fluorescence was quantified and fold ratio on control (no IFN treatment) are shown.

| ID | IFN, early | SEM | IFN, late response | NDV, 24 hr |
|---|---|---|---|---|
| GIP3-6-16 | 12.00 | 1.00 | 29.64 | 3.20 |
| PARP10-S | 12.56 | | 25.91 | 8.00 |
| MX1 | 10.82 | 0.93 | 24.63 | 7.38 |
| MX1-2 | 11.84 | 0.51 | 22.11 | 9.51 |
| VREL-1 | 15.58 | 1.25 | 21.00 | 2.30 |
| USB18-M | 10.58 | 0.78 | 20.90 | 9.35 |
| VREL-2 | 5.82 | 0.54 | 17.80 | 2.60 |
| IFIT-M1-V | 4.00 | 0.08 | 16.59 | 4.96 |
| OAS3V2 | 5.50 | | 16.24 | 15.68 |
| IFIT1 | 10.28 | 0.08 | 15.99 | 6.84 |
| VRE-G1 | 1.60 | | 14.71 | 5.10 |
| IFIT3-2 | 9.80 | 0.90 | 14.00 | 9.40 |
| SYNVRE-1 | 2.43 | | 13.23 | 7.10 |
| PARP10 | 10.87 | 0.60 | 13.00 | 3.20 |
| IFI27-1 | 0.81 | | 12.49 | 7.04 |
| IFIT3-2 S | 5.90 | 0.50 | 12.33 | 2.10 |
| VRE-G2 | 1.00 | | 12.24 | 4.00 |
| ISG-15-M | 10.70 | 0.26 | 12.21 | 3.00 |
| ISRE standard | 5.60 | 0.04 | 12.00 | 0.08 |
| SYN-ISRE-1 | 3.20 | | 11.28 | 7.00 |
| OAS3V | 7.43 | | 11.25 | 6.50 |
| STAT1 | 2.64 | 0.28 | 9.50 | 2.70 |

TABLE 3-continued

Table 3: Huh-7 cells were transfected with different constructs and then treated with IFN for brief (4-8) or longer duration (24 hr). Subsequently, fluorescence was quantified and fold ratio on control (no IFN treatment) are shown.

| ID | IFN, early | SEM | IFN, late response | NDV, 24 hr |
|---|---|---|---|---|
| ISG15-V | 1.08 | | 9.49 | 6.84 |
| SYNISRE-2 | 3.90 | | 9.03 | 8.10 |
| EPSTI1 | 6.01 | | 8.14 | 5.47 |
| USP18 | 5.72 | 0.41 | 7.93 | 2.81 |
| SYN-ISRE-2R | 1.60 | | 7.86 | 2.50 |
| PSMP9-V | 6.42 | | 7.85 | 8.57 |
| SYNVRE-2 | 1.62 | | 7.54 | 8.30 |
| NT5C3-1 | 1.97 | 0.20 | 7.46 | 4.54 |
| GAS | 3.71 | | 7.45 | 5.58 |
| IFIT2 | 5.33 | 0.50 | 7.25 | 2.80 |
| 7XVRE1 | 10.91 | 0.65 | 7.03 | 3.11 |
| TAP1 | 1.13 | | 6.65 | 2.80 |
| 7VRE2 | 8.92 | 0.83 | 5.90 | 2.94 |
| IFNA-V | 0.93 | 0.30 | 5.81 | 0.98 |
| PSMP8 | 8.29 | 1.27 | 5.63 | 2.08 |
| PRD2X | 4.03 | 0.72 | 5.51 | 4.14 |
| CASP7-1 | 1.94 | 0.62 | 4.87 | 0.84 |
| IFI44 | 3.80 | 0.52 | 4.70 | 1.97 |
| HERC5 | 3.75 | 0.22 | 4.57 | 7.75 |
| B VRE 3X | 4.26 | | 4.00 | 9.00 |
| AB-VRE-M2 | 3.74 | | 4.00 | 9.00 |
| AB-VRE | 3.07 | 0.58 | 3.75 | 5.10 |
| DDX58 | 3.02 | 0.22 | 3.02 | 2.97 |
| AB-VRE-M | 3.28 | | 3.00 | 7.00 |
| VREL-3 | 3.26 | 0.13 | 2.99 | 2.51 |
| GBP-GAS | 2.20 | 0.14 | 2.94 | 0.72 |
| IFIT-M | 1.31 | 0.20 | 2.64 | 4.10 |
| AB-VRE-M3 | 3.99 | 0.16 | 2.48 | 2.50 |
| GPB3-AV | 1.06 | | 2.20 | 0.90 |
| VRE-2B | 0.60 | | 2.12 | 1.90 |
| IFNO-V | 0.67 | 0.07 | 2.09 | 2.39 |
| IFIT3-1 | 1.85 | 0.10 | 2.01 | 5.00 |
| A VRE 3X | 1.87 | | 2.00 | 3.00 |
| CXCL10A | 2.02 | | 1.96 | 2.07 |
| OAS3V2 | | | 1.95 | 2.40 |
| PLSCR1V | 1.36 | | 1.89 | 1.07 |
| CASP7-2 | 1.21 | 0.20 | 1.82 | 1.03 |
| ISRE-2B | 1.60 | | 1.80 | 1.10 |
| TMEM67-V | 1.80 | | 1.68 | 0.94 |
| IRF-G | 0.80 | | 1.55 | 1.40 |
| GPB1-V | 1.36 | 0.31 | 1.50 | 1.68 |
| SAMD9 | 0.59 | 0.26 | 1.42 | 0.60 |
| PKR-V | 1.39 | 0.63 | 1.40 | 0.63 |
| MYD88-74 | 1.49 | | 1.36 | 1.60 |
| MATR3-2 | 1.75 | 0.47 | 1.35 | 0.24 |
| CASP7-4 | 2.12 | 0.38 | 1.35 | 0.49 |
| GAS-2 | 1.18 | | 1.30 | 1.18 |
| IRF3 | 0.90 | 0.12 | 1.24 | 0.70 |
| NT5C3-2 | 1.02 | 0.08 | 1.22 | 0.53 |
| DZIP1(2) | 1.06 | 0.10 | 1.21 | 0.78 |
| IFNB-2 | 5.27 | | 1.19 | 1.19 |
| IFI27-2V | 0.84 | | 1.18 | 1.03 |
| CXCL10B | 1.23 | | 1.17 | 1.25 |
| TMEM67 | 0.74 | 0.20 | 1.15 | 0.92 |
| IRF-7-V | 1.80 | | 1.12 | 0.89 |
| 4X-GAS-2 | 1.30 | 0.12 | 1.11 | 0.90 |
| MATR3-3 | 1.13 | 0.15 | 1.07 | 0.85 |
| IFIHI | 1.11 | 0.30 | 1.06 | 0.43 |
| IFNA5 | 0.87 | 0.08 | 1.05 | 0.79 |
| OASI | 1.87 | 0.80 | 1.01 | 1.31 |
| IFNB | 1.21 | | 1.00 | 1.05 |
| OAS1-V | 1.43 | | 1.00 | 0.76 |
| NT5C3-3 | 0.76 | 0.22 | 0.99 | 0.97 |
| RGS20-V | 0.31 | 0.10 | 0.99 | 0.93 |
| 4X GAS | 1.30 | 0.23 | 0.98 | 1.27 |
| MATR3-1 | 1.19 | 0.28 | 0.97 | 1.34 |
| C13ORF18-V | 0.70 | 0.15 | 0.93 | 1.22 |
| CASP7-3 | 0.67 | 0.13 | 0.92 | 0.42 |
| IFIT2-V | 9.93 | | 0.91 | 1.35 |
| IFIT2-V L | 1.07 | | 0.91 | 1.35 |

TABLE 3-continued

Table 3: Huh-7 cells were transfected with different constructs and then treated with IFN for brief (4-8) or longer duration (24 hr). Subsequently, fluorescence was quantified and fold ratio on control (no IFN treatment) are shown.

| ID | IFN, early | SEM | IFN, late response | NDV, 24 hr |
|---|---|---|---|---|
| GPB3-BV | 2.02 | | 0.90 | 0.88 |
| IRF-9-74 | 1.13 | | 0.88 | 1.15 |
| IFNA4 | 1.79 | 0.29 | 0.87 | 1.36 |
| C10O | 8.32 | | 0.87 | 0.94 |
| ORF18 | | | | |
| IFNA-17 | 1.45 | 0.37 | 0.86 | 1.40 |
| NFKBI | 1.53 | | 0.85 | 1.02 |
| USB18-V | 1.22 | | 0.82 | 1.09 |
| DZIP1 | 0.79 | 0.05 | 0.80 | 0.70 |
| PKR-1 | 0.84 | 0.25 | 0.74 | 0.88 |
| 3X GAS | 1.60 | 0.26 | 0.73 | 1.34 |
| VRE CON | 1.40 | 0.09 | 0.60 | 1.71 |
| SELPLG-M | 1.89 | 0.81 | 0.56 | 1.32 |
| ISG15 | 2.63 | 0.21 | 0.42 | 0.63 |
| IFI44-2 | 1.30 | 0.23 | 0.40 | 0.59 |
| CI3ORF18 | 0.81 | | 0.37 | 0.81 |
| CI3ORF18 | 0.88 | 0.40 | 0.37 | 0.81 |

Several sequences caused the EGFP reporter to respond strongly to NDV when compared to IFN including the natural GBP1-V (SEQ ID NO:13) and IFIT3-1 sequence (SEQ ID NO:12), and the synthetic VRE-Con (SEQ ID NO:14) and AB-VRE sequences (SEQ ID NO:58) (FIG. 8 and Table 1). The strongest effect of reporter induction by NDV (15-20 fold) was observed in case of sequences derived from OAS3 promoter (SEQ ID NO:15, SEQ ID NO:16), but they were not selective as they are also induced by IFN. These responses are most likely due to NDV-induced endogenous IFN production that subsequently activates the IFN responsive promoters.

Figure 9:
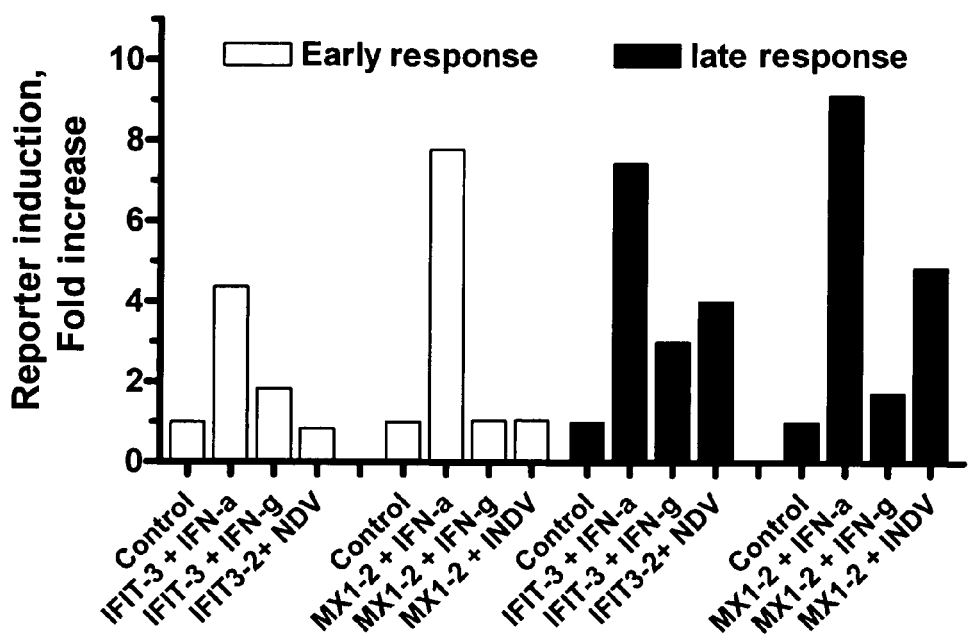
FIG. 9 Early and late expression of IFN and New Castle disease virus induced activity. Huh-7 cells ($2 \times 10^4$) were seeded in 96-well microplates and transfected with 50 ng/well of the indicated ISRE/VRE GFP reporter constructs for 16 hr. IFN (100 IU/ml) or NDV (10 HA per well) were added for 16 hr; fluorescence were quantitated from captured high resolution images using high-throughput BD bioimager and ProxCell algorithm.

There are also differential responses among different VRE/ISRE towards IFN during both early (4-8 hr) and late response (16-20 hr) as shown in FIGS. 8 and 9. The early response ranges from no IFN-induced fluorescence to strong response such as in the case of ISG15V and MX1-2 elements, respectively. Most of the virus-induced response appears as a later response; for example, responses to IFIT3-2 and MX1-2 elements-fused reporter were seen at a later time (16 hr) and was absent at the early time (6 hr; FIG. 9). Using these same sequence elements, there was strong early response to IFN-α, but in comparison, late and weak response to IFN-y (FIG. 9).

Example 5

Figure 10:
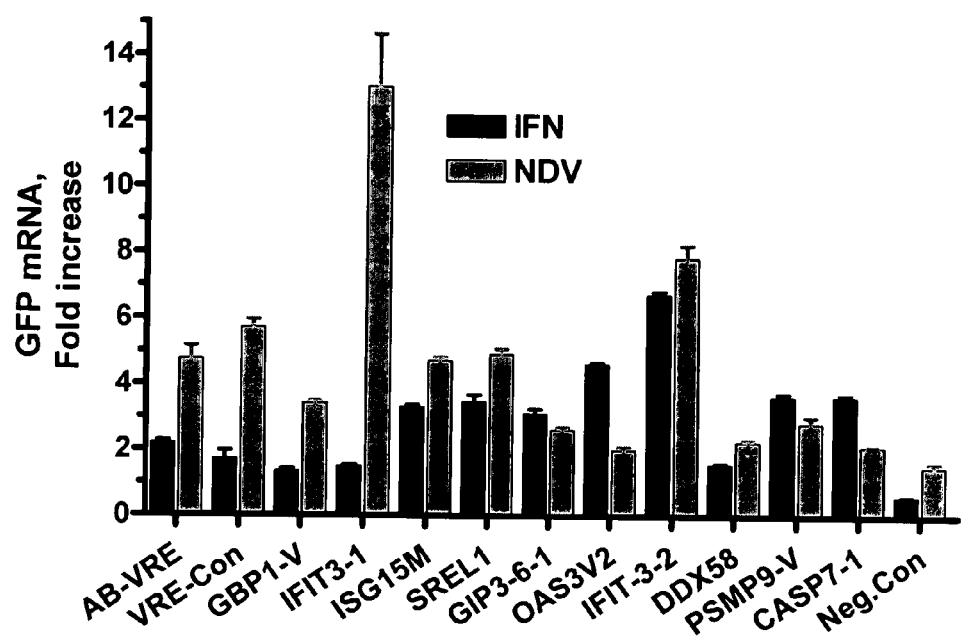
FIG. 10 QPCR evaluation of reporter activity. Huh-7 cells were challenged with the IFN and virus as previously described in FIG. 6 legend. Total RNA was subjected to RTQPCR using specific primer/TaqMan probe specific to the EGFP mRNA.

Using QPCR, reporter mRNA levels were evaluated after transfection and expression of selected constructs (FIG. 10) AB-VRE, VRE-Con, GBP1-V, IFIT3-1, ISG15M, VREL1, GIP3-6-1, OAS3V2, IFIT-3-2, DDX58, PSMP9-V, CASP7-1. Those sequences that were selective for NDV at the protein fluorescence levels, were also the case at the mRNA levels (FIG. 10). The other sequences that were selective by IFN induction at the protein levels were not so at the mRNA levels. This may be due to the different mRNA and protein kinetics and involvement of coupled transcriptional/post-transcriptional effects due to specific IRF and sequence elements interactions. However, the endpoint assay of this approach is at fluorescence levels which is the most differential and simpler approach when compared to mRNA levels.

Example 6

Figure 11:
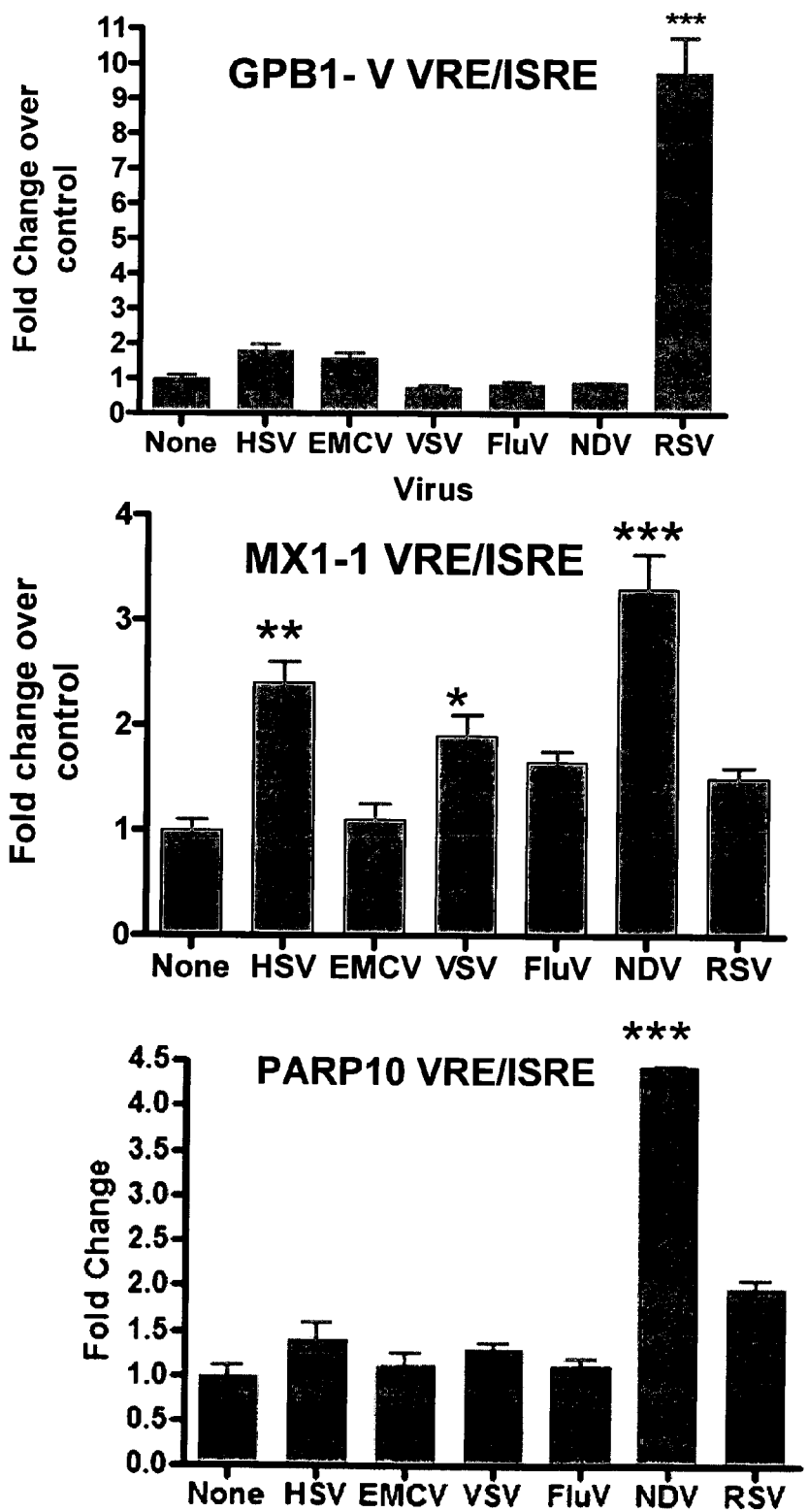
FIG. 11 Virus response sub-array. Reporter constructs that were differentially responsive to NDV and IFN, were further examined for responses to several types of viruses.

Based on the live cell fluorescence Pattern in IFN and NDV response, a subarray consisting of two to 13 constructs representing those differential virus response Patterns (FIG. 6) from a list that contains the following: AB VRE, AB-VRE-M2, B VRE 3X, GIP36-16, GPB1-V, IFIT3-1, IFIT3-2, IFNA-V, ISRE-74, MX-1, OAS3V, OAS3V2, PARP10S, SYN-ISRE-1, SYNVRE-1, SYNVRE-2, VRE Con, VRE-G1, VREL-1, VREL-2, VRE-G2, IFIT3-2S, SYN-ISRE-2R, ISGF15-M was utilized, for use with other types of viruses including both DNA and RNA viruses (FIG. 11). The GPB1-V sequence is largely of virus response with selective strong effect seen with respiratory syncytial virus (RSV; FIG. 11). On the other hand, NDV but not other viruses were able to induce reporter fluorescence due to sequence elements derived from PARP10 gene promoter. Other viruses did not induce any reporter fluorescence but several viruses were able to induce moderate levels of reporter fluorescence (FIG. 11). Thus, the cell-based multiple IFN/Virus response GFP reporter array offers research tool that is versatile and flexible to monitor and study the various anti-viral proteins such IFNs and different viruses. The data shows that heterogeneity and context sequence of the ISRE and VRE sequences influences both the strength and selectivity of responses. The use of GFP reporter allows further flexibility by monitoring at different time points, i.e., without experimental termination or cell lysis. This is also advantages in dissecting early and late responses which can used to distinguish between IFN and virus responses. Among the multiple IFN/Virus response reporters described here or from other promoter using the described approach, one can choose one or selected set for a specific IFN trigger or virus.

REFERENCES al-Haj, L., Al-Ahmadi, W., Al-Saif, M., Demirkaya, O. & Khabar, K. S. Cloningfree regulated monitoring of reporter and gene expression. BMC Mol Biol 10, 20 (2009).

Borden, E. C. et al. Interferons at age 50: past, current and future impact on biomedicine. Nut Rev Drug Discov 6, 975-990 (2007).

Fray M D, Mann G E, Charleston B. 2001 Validation of an Mx/CAT reporter gene assay for the quantification of bovine type-I interferon. J Immunol Methods. 249(1-2): 235-44.

Halees, A. S., Leyfer, D. & Weiig, Z. PromoSer: a large-scale mammalian promoter and transcription start site identification sewice. Nucleic Acids Res 31, 3554-3559 (2003).

Hitti, E. et al. A versatile ribosomal protein promoter-based reporter system for selective assessment of RNA stability and post-transcriptional control. RNA 16, 1245-1255 (2010).

Khabar, K. S. et al. Expressed gene clusters associated with cellular sensitivity and resistance towards anti-viral and anti-proliferative actions of interferon. J Mol Biol 342, 833-846 (2004).

Li, X. et al. Generation of destabilized green fluorescent protein as a transcription reporter. J Biol Chem 273, 34970-34975 (1998).

Lleonart, R., Naf, D., Browning, H., and Weissmann, C. (1990). A novel, quantitative bioassay for type I interferon using a recombinant indicator cell line. Biotechnology (N Y) 8(12), 1263-7.

Paun, A. & Pitha, P. M. The IRF family, revisited. Biochimie 89, 744-753 (2007).

Pierre, G, Alexandra, V. & Ahmet, C. The role of differential expression of human interferon—A genes in antiviral immunity. Cytokine & growth factor reviews 20, 283-295 (2009).

Sato, M., Taniguchi, T. & Tanaka, N. The interferon system arid interferon regulatory factor transcription factors—studies from gene knockout mice. Cytokine Growth Factor Rev 12, 133-142 (2001).

Savitsky, D., Tamura, T., Yanai, H. & Taniguchi, T. Regulation of immunity and oncogenesis by the IRF transcription factor family. Cancer Immunology, Immunotherapy 59, 489-510 (2010).

The invention claimed is:

1. An expression active reporter construct, comprising a response element, a transcriptional control element, a reporter DNA sequence, and a termination sequence, wherein the response element is an interferon-stimulated response element (ISRE) or a virus response element (VRE) comprising any one of SEQ ID NOs: 4-24.

2. The reporter construct according to claim 1, wherein the response element is attached to a flanking region of 20-100 nucleotides.

3. The reporter construct according to claim 1, wherein the transcriptional control element comprises a minimal promoter which comprises at least a TATAA or TATAA-like signal, a GC-Box, CAAT signal, and/or an AP-1 site.

4. The reporter construct according to claim 3, wherein the minimal promoter comprises a minimal CMV promoter, a HSV TK promoter, a SV40 promoter, a synthetic minimal promoter, a viral or cellular promoter, or an inducible promoter.

5. The reporter construct according to claim 4, wherein the transcriptional control element comprises a minimal CMV IE promoter from position −36, −53, or −74 from the transcriptional start site.

6. The reporter construct according to claim 1, wherein the reporter DNA sequence encodes a reporter protein that is an enhanced green fluorescent protein (EGFP), an EGFP-MODC fusion protein, or luciferase.

7. The reporter construct according to claim 1, wherein the termination sequence comprises a SV40 polyadenylation signal, and/or wherein the termination sequence is the termination sequence of bovine growth hormone (BGH).

8. The reporter construct according to claim 1, wherein the expression active reporter construct comprises an intron or enhancer.

9. A stable cell line expressing a reporter protein from an expression active reporter construct according to claim 1.

10. The stable cell line according to claim 9, which is a Vero, 293T, K562, MDCK, HT1080, or HepGR, or a liver cell line.

11. An array comprising at least one expression active response reporter construct, wherein the expression active response reporter construct comprises a response element, a transcriptional control element, a reporter DNA sequence, and a termination sequence, wherein the response element is an interferon-stimulated response element (ISRE) or a virus response element (VRE) selected from SEQ ID NO: 4 to SEQ ID NO: 109.

12. The array according to claim 11, comprising at least two expression active reporter constructs, wherein at least two reporter constructs have different response elements, and wherein the sequences of the response elements are selected from SEQ ID NO: 4 to SEQ ID NO:109.

13. The array according to claim 11, comprising at least thirteen different expression active reporter constructs, wherein at least thirteen reporter constructs have different response elements, and wherein the sequences of the response elements are selected from SEQ ID NO: 4 to SEQ ID NO:109.

14. The array according to claim 11, wherein the response elements of the reporter constructs comprise at least one sequence selected from SEQ ID NO: 4, SEQ ID NO:5, SEQ ID NO: 6, SEQ ID NO:7, SEQ ID NO: 8, SEQ ID NO: 9, SEQ ID NO:10, and SEQ ID NO: 11.

15. The array according to claim 11, wherein the response elements of the reporter constructs comprise at least one sequence selected from SEQ ID NO: 12, SEQ ID NO: 13, SEQ ID NO:14, and SEQ ID NO: 58.

16. The array according to claim 11, wherein the reporter constructs have response elements that comprise SEQ ID NO: 4 (VREL-1), SEQ ID NO: 11 (PARP10), SEQ ID NO:16 (OAS3V2), and SEQ ID NO: 9 (USB18-M).

17. The array according to claim 11, wherein the reporter constructs have reporter constructs with response elements that comprise SEQ ID NO: 16 (OAS3V2), SEQ ID NO: 10 (IFIT3-2), SEQ ID NO: 4 (VREL-1), SEQ ID NO: 53 (GIP3-6-16), SEQ ID NO: 5 (VREL-2), SEQ ID NO: 12 (IFIT3-1), SEQ ID NO: 78 (GPB1-V), SEQ ID NO: 14 (VRE Con), SEQ ID NO: 58 (AB-VRE), SEQ ID NO: 62 (IFNA-V), SEQ ID NO: 33 (MX-1), SEQ ID NO: 15 (OAS3-V), and SEQ ID NO: 11 (PARP 10).

18. The array according to claim 11, wherein the reporter constructs have response elements that comprise SEQ ID NO: 104 (AB-VRE-M2), SEQ ID NO: 5 (VREL-2), SEQ ID NO: 4 (VREL-1), SEQ ID NO: 100 (VRE-G1), SEQ ID NO: 9 (USB18-M), SEQ ID NO: 101 (SYN-ISRE-2R), SEQ ID NO: 19 (PARP10-S), SEQ ID NO: 11 (PARP10), SEQ ID NO: 16 (OAS3V2), SEQ ID NO: 15 (OAS3-V), SEQ ID NO:18 (MX1-2-2), SEQ ID NO: 33 (MX1), SEQ ID NO: 62 (IFNA-V), SEQ ID NO: 23 (IFIT3-2S), SEQ ID NO: 10 (IFIT3-2), SEQ ID NO: 12 (IFIT3-1), SEQ ID NO: 24 (IFIT1), SEQ ID NO: 78 (GPB1-V), SEQ ID NO: 53 (GIP3-6-16), SEQ ID NO: 105 (AB-VRE-M), SEQ ID NO: 58 (AB-VRE), SEQ ID NO: 31 (HERC5), SEQ ID NO: 102 (SYN-ISRE-2), SEQ ID NO: 103 (B-VRE-3X), and SEQ ID NO: 74 (PSMP9-V).

19. The array according to claim 11, wherein the expression active response reporter construct is transfected into a stable cell line.

20. A method for detection of recombinant interferon induction, comprising the steps of:
providing an array with expression active reporter constructs according to claim 1,
transfection of the expression active reporter constructs into cells,
exposing cells to a recombinant interferon, and
detection of reporter activity.

21. The method of claim 20, wherein the reporter construct is in a 96-well plate or a 384-well plate.

22. A kit comprising an array according to claim 11, a buffer, and a stable cell line.

23. The kit of claim 22, further comprising an instruction sheet.

* * * * *

UNITED STATES PATENT AND TRADEMARK OFFICE
CERTIFICATE OF CORRECTION

Page 1 of 1

PATENT NO. : 9,677,071 B2
APPLICATION NO. : 14/112773
DATED : June 13, 2017
INVENTOR(S) : Khalid S. Abu Khabar and Fahad Nasser Al-Majhdi It is certified that error appears in the above-identified patent and that said Letters Patent is hereby corrected as shown below:

Column 3,
Line 14, "or 31 74 from" should read -- or -74 from --.

Column 4,
Line 45, "(B-VRE-3x)" should read -- (B-VRE-3X) --.

Column 25,
Line 50, "SEQ ID NO: 40 IPARP10-1" should read -- SEQ ID NO: 40 PARP10-1 --.
Line 55, "SEQ ID NO: 42...GIGGTTFT..." should read -- SEQ ID NO: 42...GTGGTTTT... --.

Column 31,
Line 47, "wherein S is Q" should read -- wherein S is G --.
Line 48, "and N is A, C, Q" should read -- and N is A, C, G, --.

Signed and Sealed this
Sixth Day of March, 2018

Andrei Iancu
*Director of the United States Patent and Trademark Office*